US010449202B2

(12) United States Patent
Lee et al.

(10) Patent No.: US 10,449,202 B2
(45) Date of Patent: Oct. 22, 2019

(54) RATIONALE-BASED DESIGN OF A TARGETED THERAPY FOR CANCER

(71) Applicant: Celestra Life Science LLC, Richmond, VA (US)

(72) Inventors: Allen J. Lee, Short Hills, NJ (US); Jason J. Lee, Short Hills, NJ (US); David M. Lu, Richmond, NJ (US); Ruey-Min Lee, Short Hills, NJ (US)

(73) Assignee: CELESTRA LIFE SCIENCE LLC, Richmond, VA (US)

( * ) Notice: Subject to any disclaimer, the term of this patent is extended or adjusted under 35 U.S.C. 154(b) by 0 days.

(21) Appl. No.: 15/653,480

(22) Filed: Jul. 18, 2017

(65) Prior Publication Data

US 2018/0117061 A1    May 3, 2018

Related U.S. Application Data

(63) Continuation of application No. 15/101,392, filed as application No. PCT/US2014/068373 on Dec. 3, 2014, now Pat. No. 9,782,418.

(60) Provisional application No. 61/911,423, filed on Dec. 3, 2013.

(51) Int. Cl.
*A61K 31/553* (2006.01)
*G01N 33/50* (2006.01)

(52) U.S. Cl.
CPC ........ *A61K 31/553* (2013.01); *G01N 33/5011* (2013.01)

(58) Field of Classification Search
CPC .................................................. A61K 31/553
See application file for complete search history.

(56) References Cited

U.S. PATENT DOCUMENTS

| 9,782,418 B2 * | 10/2017 | Lee ...................... A61K 31/553 |
| 2011/0275528 A1 * | 11/2011 | Meyer .................. C12Q 1/6886 506/9 |

FOREIGN PATENT DOCUMENTS

WO    WO-2015084958 A1    6/2015

OTHER PUBLICATIONS

Kohler, PloS one (2012), 7(4), e34973.*
Geng, Proceedings of the National Academy of Sciences of the United States of America (2013), 110(17), 6997-7002.*
Barbrieri, Nature Genetics 2012; 44: 685-689.*
Gnanapragasam, Br J Cancer. 2001; 85: 1928-36.*
Anzick, et al. AIB1, a steroid receptor coactivator amplified in breast and ovarian cancer. Science 277.5328 (1997): 965-968.
Barbieri, et al. Exome sequencing identifies recurrent SPOP, FOXA1 and MED12 mutations in prostate cancer. Nature genetics 44.6 (2012): 685-689.
Burandt, et al. Prognostic relevance of AIB1 (NCoA3) amplification and overexpression in breast cancer. Breast cancer research and treatment 137.3 (2013): 745-753.
Chang, et al. AWP1 binds to tumor necrosis factor receptor-associated factor 2 (TRAF2) and is involved in TRAF2-mediated nuclear factor-kappaB signaling. The international journal of biochemistry & cell biology 43.11 (2011): 1612-1620.
Collins, et al. Preclinical and clinical studies with the multi-kinase inhibitor CEP-701 as treatment for prostate cancer demonstrate the inadequacy of PSA response as a primary endpoint. Cancer biology & therapy 6.9 (2007): 1360-1367.
Duan, et al. Cloning and characterization of AWP1, a novel protein that associates with serine/threonine kinase PRK1 in vivo. Gene 256.1 (2000): 113-121.
European search report and search opinion dated Jun. 2, 2017 for EP Application No. 14867137.3.
Geng, et al. Prostate cancer-associated mutations in speckle-type POZ protein (SPOP) regulate steroid receptor coactivator 3 protein turnover. Proceedings of the National Academy of Sciences 110.17 (2013): 6997-7002.
George, et al. Sustained in vivo regression of Dunning H rat prostate cancers treated with combinations of androgen ablation and Trk tyrosine kinase inhibitors, CEP-751 (KT-6587) or CEP-701 (KT-5555). Cancer Research 59.10 (1999): 2395-2401.
Gnanapragasam, et al. Expression of RAC 3, a steroid hormone receptor co-activator in prostate cancer. British journal of cancer 85.12 (2001): 1928-1936.
Gojis, et al. The role of SRC-3 in human breast cancer. Nature reviews Clinical oncology 7.2 (2010): 83-89.
International search report and written opinion dated Apr. 29, 2015 for PCT Application No. PCT/US2014/068373.
Kapoor, S. AIB1 and its significant role in tumor pathogenesis in systemic malignancies: beyond breast carcinomas. Ann Oncol 24 (2013): 1414.
Kavanaugh, et al. The human DEK oncogene regulates DNA damage response signaling and repair. Nucleic acids research 39.17 (2011): 7465-7476.
Kim, et al. Mutational and expressional analyses of SPOP, a candidate tumor suppressor gene, in prostate, gastric and colorectal cancers. Apmis 121.7 (2013): 626-633.
Kohler, et al. Lestaurtinib inhibits histone phosphorylation and androgen-dependent gene expression in prostate cancer cells. PloS one 7.4 (2012): e34973.
Kominea, et al. Androgen receptor (AR) expression is an independent unfavorable prognostic factor in gastric cancer. Journal of cancer research and clinical oncology 130.5 (2004): 253-258.
Kwon, et al. BTB domain-containing speckle-type POZ protein (SPOP) serves as an adaptor of Daxx for ubiquitination by Cul3-based ubiquitin ligase. Journal of Biological Chemistry 281.18 (2006): 12664-12672.

(Continued)

*Primary Examiner* — Nizal S Chandrakumar
(74) *Attorney, Agent, or Firm* — Wilson Sonsini Goodrich & Rosati

(57) ABSTRACT

The methods, compositions, and kits of the invention are related to the discovery that lestaurtinib reduces levels and pathway activity of an SPOP substrate. Accordingly, described herein are methods and compositions for the use of lestaurtinib in downregulating one or more SPOP substrates or signaling pathway activities thereof in a subject in need thereof.

16 Claims, 9 Drawing Sheets

Specification includes a Sequence Listing.

(56) References Cited

OTHER PUBLICATIONS

Lee, et al. Downstream effectors of SPOP pathway and implication for prostate cancer therapy. Official abstract for the North Jersey Regional Science Fair, 2015.
Levis, et al. A FLT3-targeted tyrosine kinase inhibitor is cytotoxic to leukemia cells in vitro and in vivo. Blood 99.11 (2002): 3885-3891.
Li, et al. Tumor-suppressor role for the SPOP ubiquitin ligase in signal-dependent proteolysis of the oncogenic co-activator SRC-3/AIB1. Oncogene 30.42 (2011): 4350-4364.
Metzger, et al. A novel inducible transactivation domain in the androgen receptor: implications for PRK in prostate cancer. The EMBO journal 22.2 (2003): 270-280.
Nakano, et al. Identification of androgen-responsive microRNAs and androgen-related genes in breast cancer. Anticancer research 33.11 (2013): 4811-4819.
Notice of allowance dated Apr. 26, 2017 for U.S. Appl. No. 15/101,392.
Notice of allowance dated Jul. 7, 2017 for U.S. Appl. No. 15/101,392.
Piao, et al. High expression of DEK predicts poor prognosis of gastric adenocarcinoma. Diagnostic pathology 9.1 (2014): 67.
Sakakura, et al. Amplification and over-expression of the AIB1 nuclear receptor co-activator gene in primary gastric cancers. International journal of cancer 89.3 (2000): 217-223.
Vinnedge, et al. The DEK oncogene is a target of steroid hormone receptor signaling in breast cancer. PloS one 7.10 (2012): e46985.
Xu, et al. Normal and cancer-related functions of the p160 steroid receptor co-activator (SRC) family. Nature Reviews Cancer 9.9 (2009): 615-630.
Zhang, et al. A hedgehog-induced BTB protein modulates hedgehog signaling by degrading Ci/Gli transcription factor. Developmental cell 10.6 (2006): 719-729.
Zhang, et al. Multiple Ser/Thr-rich degrons mediate the degradation of Ci/Gli by the Cul3-HIB/SPOP E3 ubiquitin ligase. Proceedings of the National Academy of Sciences 106.50 (2009): 21191-21196.
Zhou, et al. SRC-3 is required for prostate cancer cell proliferation and survival. Cancer Research 65.17 (2005): 7976-7983.
Zhuang, et al. Structures of SPOP-Substrate Complexes: Insights into Molecular Architectures of BTB-Cul3 Ubiquitin Ligases. Mol Cell. Oct. 9, 2009; 36(1): 39-50. doi:10.1016/j.molcel.2009.09.022.

* cited by examiner

FIG 2A. PC3 (IC$_{50}$>3 μM for lestaurtinib, IC$_{50}$=0.07 μM for staurosporine (STS))
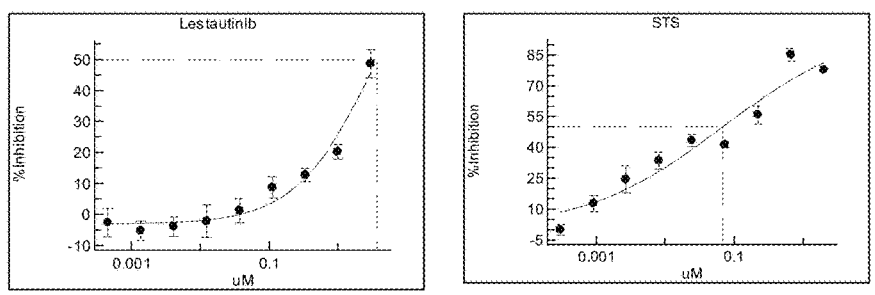
FIG 2B. 22RV1 (IC$_{50}$=0.36 μM for lestaurtinib, IC$_{50}$=0.02 μM for staurosporine (STS))
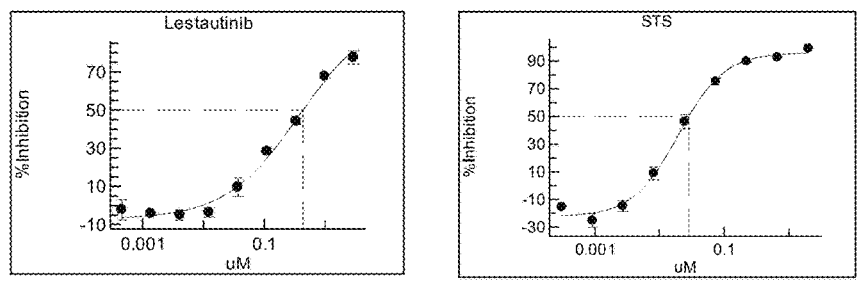
FIG 2C. LNCaP clone FGC: (IC$_{50}$=0.32 μM for lestaurtinib, IC$_{50}$=0.09 μM for staurosporine (STS))
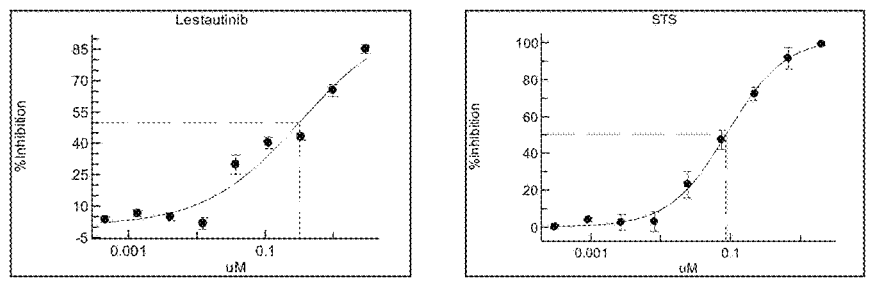

FIG 3A. MCF7 (IC$_{50}$=1.15 µM for lestaurtinib, IC$_{50}$=0.02 µM for staurosporine (STS))
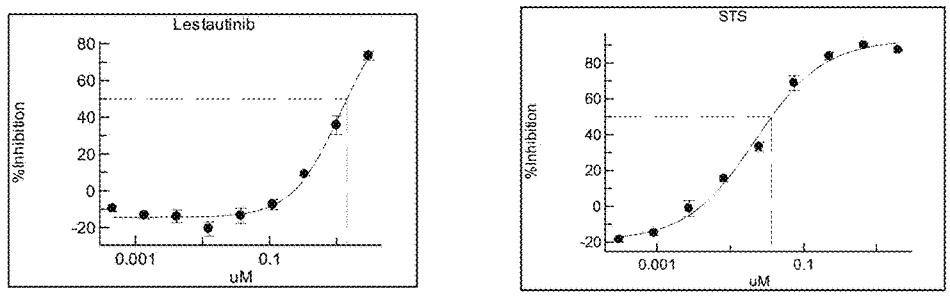
FIG 3B. BT-474 (IC$_{50}$ >3 µM for lestaurtinib, IC$_{50}$=0.21 µM for staurosporine (STS))
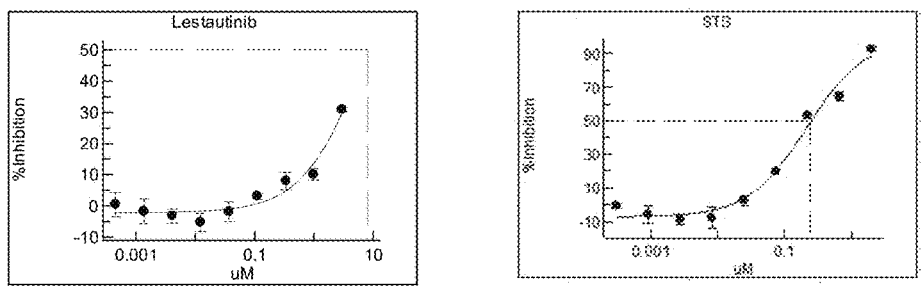
FIG 3C. ZR-75-1 (IC$_{50}$ =1.95 µM for lestaurtinib, IC$_{50}$=0.22 µM for staurosporine (STS))
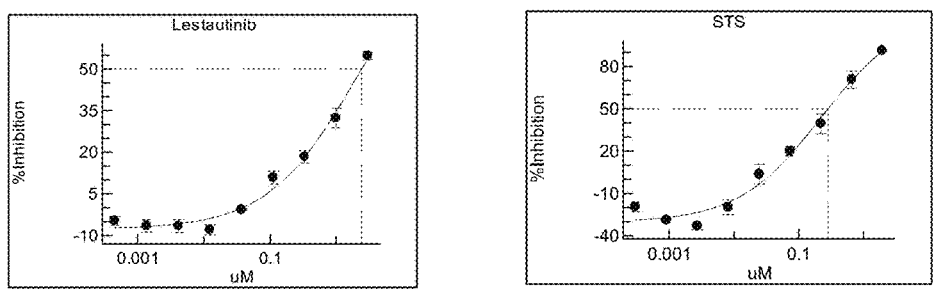

FIG 4A. AGS (IC$_{50}$ =0.39 µM for lestaurtinib, IC$_{50}$=0.01 µM for staurosporine (STS))
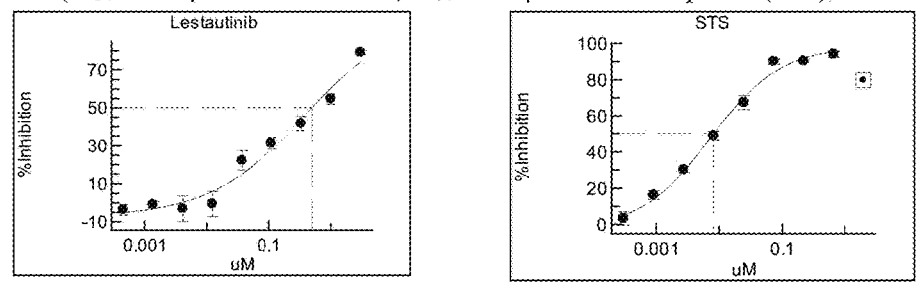
FIG 4B. MKN-45 (IC$_{50}$ =0.31 µM for lestaurtinib, IC$_{50}$=0.02 µM for staurosporine (STS))
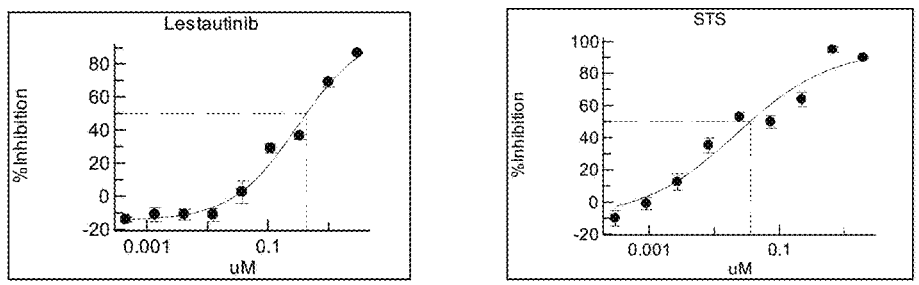
FIG 4C. Hs746T (IC$_{50}$ =0.87 µM for lestaurtinib, IC$_{50}$=0.05 µM for staurosporine (STS))
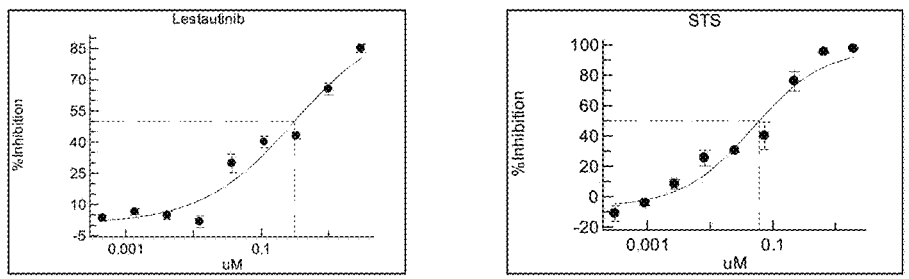
FIG 4D. NCI-N87 (IC$_{50}$ =0.88 µM for lestaurtinib, IC$_{50}$=0.01 µM for staurosporine (STS))
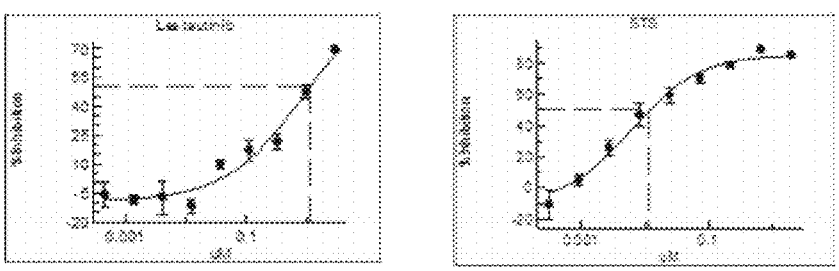

Summary of IC$_{50}$ results for all cell lines tested

|  |  | IC$_{50}$(μM) | |
|---|---|---|---|
|  | Cells | Lestautinib | Staurosporine |
| Prostate cancer cells | PC-3 | >3.0 | 0.07 |
|  | 22RV1 | 0.36 | 0.02 |
|  | LNCaP Clone FGC | 0.32 | 0.09 |
| Breast cancer cells | MCF7 | 1.15 | 0.02 |
|  | BT-474 | >3.0 | 0.21 |
|  | ZR-75-1 | 1.95 | 0.22 |
| Gastric cancer | AGS | 0.39 | 0.01 |
|  | MKN-45 | 0.31 | 0.02 |
|  | Hs746T | 0.87 | 0.05 |
|  | NCI-N87 | 0.88 | 0.01 |

FIG. 5

FIG. 8A. Western blotting
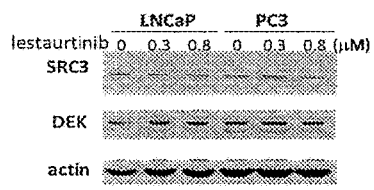
FIG. 8B SRC3 expression relative to actin
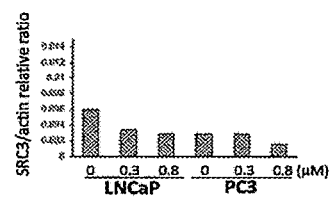
FIG. 8C DEK expression relative to actin
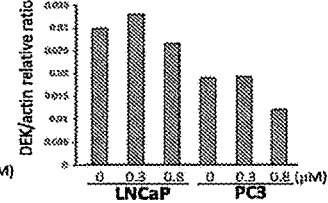
FIG. 9A. Western blotting
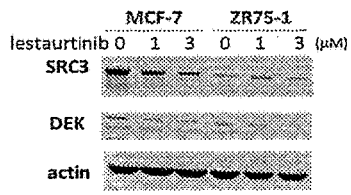
FIG. 9B SRC3 expression relative to actin
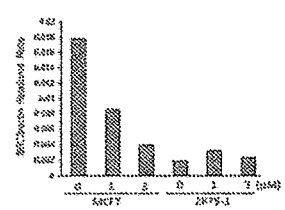
FIG. 9C DEK expression relative to actin
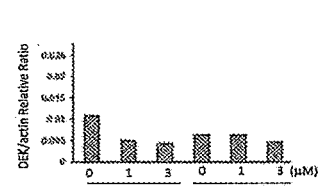
FIG. 10A. Western blotting
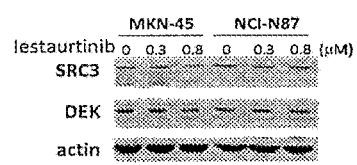
FIG. 10B. SRC3 expression relative to actin
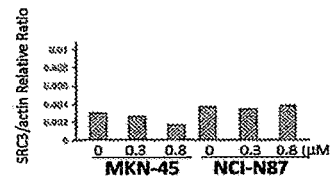
FIG. 10C. DEK expression relative to actin
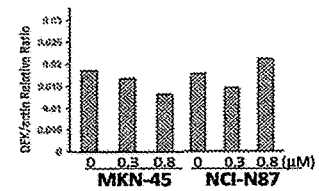

GenBank Accession CAA04199:

MSRVPSPPPPAEMSSGPVAESWCYTQIKVVKFSYMWTINNFSFCREEMGEVIKSSTFSSG
ANDKLKWCLRVNPKGLDEESKDYLSLYLLLVSCPKSEVRAKFKFSILNAKGEETKAMESQ
RAYRFVQGKDWGFKKFIRRDFLLDEANGLLPDDKLTLFCEVSVVQDSVNISGQNTMNMVK
VPECRLADELGGLWENSRFTDCCLCVAGQEFQAHKAILAARSPVFSAMFEHEMEESKKNR
VEINDVEPEVFKEMMCFIYTGKAPNLDKMADDLLAAADKYALERLKVMCEDALCSNLSVE
NAAEILILADLHSADQLKTQAVDFINYHASDVLETSGWKSMVVSHPHLVAEAYRSLASAQ
CPFLGPPRKRLKQS

FIG. 11

RATIONALE-BASED DESIGN OF A TARGETED THERAPY FOR CANCER

CROSS-REFERENCE

This application is continuation application of U.S. patent application Ser. No. 15/101,392, filed Jun. 2, 2016, now U.S. Pat. No. 9,782,418, which is a national stage entry of International Application No. PCT/US2014/68373, filed Dec. 3, 2014, which claims priority from U.S. Provisional Application No. 61/911,423, filed Dec. 3, 2013, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 2, 2017 is named 45824_701_301_SL updated Jan. 2, 2018 and is 16,467 bytes in size.

BACKGROUND OF THE INVENTION

Ubiquitin-mediated protein degradation generally occurs via the ubiquitin proteosome pathway. In this pathway, ubiquitin-protein ligases (e.g., E3 ligases) target selected proteins for degradation by ligating ubiquitin chains to the proteins to be degraded. Ubiquitination enables the proteins to then be recognized by a proteosome complex, which then degrades the proteins. Speckle type POZ protein (SPOP) has been implicated in the ubiquitin-mediated degradation of target proteins by serving the function of substrate recognition.

SPOP generally comprises two domains: a MATH domain and a poxvirus and zinc finger (POZ) domain, alternatively referred to as a BTB domain. The general structure of SPOP is illustrated in FIG. 1. SPOP proteins typically recruit protein substrates (e.g., SPOP substrates) to E3 ubiquitin ligases via its MATH and POZ domains. SPOP substrates typically complex with the MATH domain of SPOP proteins, while Cullin-3 E3 ubiquitin ligase interacts with the POZ domain. SPOP-mediated recruitment of SPOP substrates to Cullin-3 type E3 ubiquitin ligase facilitates E3-mediated ubiquitination of SPOP substrates, thus targeting the substrates for proteosomal degradation.

Exome sequencing of human prostate tumors revealed that a subset of prostate tumors comprise SPOP mutations (Nature Genetics 2012; 44: 685-689, hereby incorporated by reference). Altogether, SPOP mutations were found to be present in 6-15% of prostate tumors in the study (Nature Genetics 2012; 44: 685-689). Interestingly, all of the identified SPOP mutations associated with prostate tumors were within the substrate-binding pocket of SPOP (Nature Genetics 2012; 44: 685-689), indicating that such mutations may impair SPOP substrate binding and subsequent ubiquitination (Proc Natl Acad Sci USA. 2013 110: 6997-7002, hereby incorporated by reference). It was reported that SRC-3 protein was overexpressed in 38% of tumor samples of prostate cancer (Br J Cancer. 2001; 85: 1928-36, hereby incorporated by reference). Another study showed that SRC-3 expression is required for prostate cancer cell proliferation and survival, and its levels correlated with Prostate Specific Antigen (PSA). In a batch of prostate cancer samples from patients with prostectomy, tumor with high expression of SRC3 was shown to be correlated with lower recurrence free survival (Cancer Res. 2005 Sep. 1; 65(17): 7976-83, hereby incorporated by reference). These studies suggest an important role of SRC-3 in prostate cancer formation and as a poor prognostic factor. Furthermore, SPOP mutations associated with prostate cancer impede the ability of SPOP to induce ubiquitin-dependent degradation of SRC-3 (Proc Natl Acad Sci USA. 2013 110: 6997-7002). SRC3 has also been shown to be amplified in breast cancer, both at the gene level and at the transcript level (Nature Reviews Clinical Oncology 2010; 7:83-89, hereby incorporated by reference). For example, in one study, 58% of breast tumor biopsies exhibit elevated SRC3 gene expression levels. Elevated SRC3 levels are also associated with a number of other cancers. In addition to breast cancer and prostate cancer, elevated SRC3 levels were demonstrated in pancreatic cancer and gastric cancer.

Mutational and expressional analysis of SPOP was done by Kim et al. (APMIS. 2013; 121: 626-33) in 45 gastric cancer, 45 colorectal cancer and 45 prostate cancer samples by single-strand conformation polymorphism (SSCP). In addition, they also analyzed SPOP protein expression in 60 gastric cancer, 60 colorectal cancer and 60 prostate cancer tumor specimens by immunohistochemistry. Three somatic missense mutations (2 in prostate cancer and one in colorectal cancer) of SPOP gene in the coding sequences (Ser14Leu, Tyr87Cys and Phe133Leu) were all located in the N-terminal substrate-binding domain. In the immunohistochemistry, SPOP protein was expressed in normal gastric, colonic and prostate epithelial cells, whereas loss of SPOP was found in 30% of gastric cancer, 20% of colorectal cancer and 37% of prostate cancer.

SRC3 also plays a critical role in breast cancer and other malignancies (Science 1997; 277: 965-8, Ann Oncol. 2013; 24: 1414). In a study reported by Burandt (Breast Cancer Res Treat. 2013 137:745-53), 2,197 breast carcinomas samples were analyzed and SRC3 overexpression by gene profiling and immunohistochemistry (IHC) was associated with tumor size, high histological grade, poor disease-specific, and overall survival. AIB1 amplification by fluorescent-in-situ hybridization (FISH) was found in 11% of the carcinomas. It was associated with high histological grade, lymph node involvement, and poor disease-specific survival (Breast Cancer Res Treat. 2013 137:745-53).

SRC3 amplification was observed in 7%, and over-expression in 40% of gastric cancer specimens (Int J Cancer. 2000; 89:217-23). SRC3 amplification usually coincided with its over-expression, and associated with poor prognosis. Interestingly, 15/86 (17.4%) cases of gastric adenocarcinomas were positive for Androgen Receptor (J. Can. Res. Clin. Onc. 2004; 130: 253-258). Patients with AR-positive tumors (AR+) had significantly worse prognosis than (AR−) patients (median survival 9 months vs 24 months, P=0.03).

One new estrogen receptor (ER) target was identified as DEK, whose expression also promotes estrogen-induced proliferation in breast cancer cells. DEK depletion enhances tamoxifen-induced cell death in ER+ breast cancer cell lines (PLoS ONE 2012; 7: e46985). DEK was previously identified as a DNA remodeling protein. DEK regulates DNA damage response and signaling repair. DEK functions as a transcriptional factor and is also reported to be an oncogene and ubiquitously expressed in nearly all organ and tumors (Nucleic Acids Res. 2011; 39: 7465-76). DEK protects tumor cells from DNA damaging agents and cell death via p53-dependent and -independent mechanisms by facilitating DNA double-strand break repair. High expression of DEK was associated with poor prognosis in gastric cancer (Diagn. Pathol. 2014; 9: 67).

Lestaurtinib is an indolocarbazole derivative that was originally found as an inhibitor of various receptor kinases, including JAK2 ($IC_{50}$=0.9 nM), PDGFβ ($IC_{50}$=216 nM), STAT3 ($IC_{50}$=10-30 nM), TRKB ($IC_{50}$=<25 nM), PRK1 ($IC_{50}$=8.6 nM), and PKC ($IC_{50}$=226 nM) and FLT3 (Cancer Res. 1999; 59: 2395-401, Blood. 2002; 99: 3885-91, which are hereby incorporated by reference). Due to its receptor kinase inhibitory activity, lestaurtinib was proposed as a potential therapeutic agent for prostate cancer. However, a Phase 2 human clinical trial demonstrated that treatment of prostate cancer patients with lestaurtinib failed to achieve the primary clinical endpoint of reduced PSA levels (Cancer Biol Ther. 2007; 6: 1360-7, hereby incorporated by reference). Thereafter, very limited clinical development has been ongoing for lestaurtinib.

SUMMARY OF THE INVENTION

The methods, compositions, and kits of the invention are related to the discovery that lestaurtinib can reduce expression levels and/or pathway activity of an SPOP substrate or that of its downstream target.

Accordingly, the invention provides a method of downregulating a speckle-type POZ protein (SPOP) substrate signaling in a subject in need thereof, comprising administering to the subject a pharmaceutical composition comprising a therapeutically effective amount of lestaurtinib or pharmaceutically acceptable salt thereof, thereby downregulating the SPOP substrate signaling in the subject.

In some embodiments, the substrate is selected from the group consisting of SRC1, SRC2, SRC3, Daxx, Gli, AWP-1, cullin-4B, cullin-7, and DEK. In some embodiments, the substrate is SRC1, SRC2, or SRC3. In some embodiments, the substrate is SRC3. In some embodiments, the substrate is DEK.

In some embodiments, the downregulating comprises decreasing a level and/or activity of the SPOP substrate or downstream target of the substrate. In some embodiments, the downregulating is evidenced by a reduction in activity of the downstream target in a cell derived from the subject. In some embodiments, the downstream target is PRK-1. In some embodiments, the downregulating comprises decreasing a level and/or activity of the SPOP substrate. In some embodiments, the downregulating is evidenced by a reduction in a level of the substrate in a cell derived from the subject. In some embodiments, the level comprises an expression level. In some embodiments, the expression level is a protein expression level. In some embodiments, the expression level is evidenced by a level of a transcript of the SPOP substrate. In some embodiments, the downregulating is evidenced by a reduction in a level of the substrate in a cytoplasmic fraction of the cell.

The invention also provides a method of treating a prostate tumor in a subject in need thereof, comprising: administering to the subject a first dose of a pharmaceutical composition comprising a therapeutically effective amount of lestaurtinib or pharmaceutically acceptable salt thereof determining an SPOP substrate level or its activity in a biological sample derived from the subject; and administering an additional dose of the pharmaceutical composition if the substrate level or its activity is reduced as compared to a control subject that is not administered a pharmaceutical composition comprising a therapeutically effective amount of lestaurtinib or pharmaceutically acceptable salt thereof.

The invention also provides a method of treating a prostate tumor in a subject, comprising administering to the subject a pharmaceutical composition comprising a therapeutically effective amount of lestaurtinib or pharmaceutically acceptable salt thereof, wherein the subject exhibits an aberrantly high level of an SPOP substrate or its activity as compared to a control subject.

In some embodiments, the aberrantly high level is evidenced by presence of an SPOP mutation in the tumor. In some embodiments, the mutation results in an altered amino acid sequence between positions 31-161 of the SPOP amino acid sequence. In some embodiments, the altered amino acid sequence comprises an amino acid substitution. In some embodiments, the mutation causes a substitution at Y87, F102, S119, F125, K129, W131, F133, and/or K134 of the SPOP amino acid sequence. In some embodiments, the mutation causes a Y87C substitution, a Y87N substitution, an F102C substitution, an S119N substitution, an F125V substitution, a K129N substitution, a W131G substitution, an F133L substitution, an F133V substitution, or any combination of substitutions thereof.

In practicing any of the methods herein, the subject can be a human. In some embodiments, the subject evidences a symptom of a disease. In some embodiments, the disease is a prostate disease. In some embodiments, the disease is a prostate tumor. In some embodiments, the prostate tumor is androgen sensitive. In some embodiments, the prostate tumor is androgen insensitive. In some embodiments, the prostate tumor is estrogen sensitive. In some embodiments, the prostate tumor is estrogen insensitive. In some embodiments, the disease is a breast or gastric disease. In some embodiments, the disease is a breast or gastric tumor. In some embodiments, the breast or gastric tumor is androgen sensitive. In some embodiments, the breast or gastric tumor is androgen insensitive. In some embodiments, the breast or gastric tumor is estrogen sensitive. In some embodiments, the breast or gastric tumor is estrogen insensitive.

The invention also provides a method of downregulating an SPOP substrate level or its activity in a prostate cell, comprising: administering to the cell an effective amount of lestaurtinib, thereby downregulating the SPOP substrate or its activity in the cell; and assessing downregulation of the SPOP substrate level or its activity in the prostate cell.

In some embodiments, the prostate cell is a prostate cancer cell. In some embodiments, the prostate cell is a cultured cell. In some embodiments, the prostate cell is an androgen-sensitive prostate cell. In some embodiments, the prostate cell is an estrogen-sensitive prostate cell. In some embodiments, the prostate cell is an LNCaP cell.

The present further provides a method of downregulating an SPOP substrate level or its activity in a breast or gastric cell, comprising: (a) administering to the cell an effective amount of lestaurtinib, thereby downregulating the SPOP substrate or its activity in the cell; and (b) assessing downregulation of the SPOP substrate level or its activity in the breast or gastric cell.

In a separate but related embodiment, the present invention provides method of treating a breast or gastric tumor in a subject in need thereof, comprising: (a) administering to the subject a first dose of a pharmaceutical composition comprising a therapeutically effective amount of lestaurtinib or pharmaceutically acceptable salt thereof (b) determining an SPOP substrate level or its activity in a biological sample derived from the subject; and (c) administering an additional dose of the pharmaceutical composition if the substrate level or its activity is reduced as compared to a control subject that is not administered a pharmaceutical composition comprising a therapeutically effective amount of lestaurtinib or pharmaceutically acceptable salt thereof.

In yet another embodiment, the present invention provides a method of treating a breast or gastric tumor in a subject, comprising administering to the subject a pharmaceutical composition comprising a therapeutically effective amount of lestaurtinib or pharmaceutically acceptable salt thereof, wherein the subject exhibits an aberrantly high level of an SPOP substrate or its activity as compared to a control subject.

In still yet another embodiment, the present invention provides a method of treating a breast or gastric tumor in a subject in need thereof, comprising: (a) administering to the subject a first dose of a pharmaceutical composition comprising a therapeutically effective amount of lestaurtinib or pharmaceutically acceptable salt thereof (b) determining an SPOP substrate level or its activity in a biological sample derived from the subject; and (c) administering an additional dose of the pharmaceutical composition if the substrate level or its activity is reduced as compared to a control subject that is not administered a pharmaceutical composition comprising a therapeutically effective amount of lestaurtinib or pharmaceutically acceptable salt thereof.

In some embodiments, the breast or gastric cell is a cancerous primary or otherwise cultured breast or gastric cell. In some embodiments, the breast or gastric cell is an androgen-sensitive or estrogen-sensitive cell. In some embodiments, the breast cell is an MCF7 cell. In some embodiments, the substrate is selected from the group consisting of SRC1, SRC2, SRC3 (Oncogene 2011; 30:4350-64) (Nat Rev Cancer. 2009; 9: 615-30, which are hereby incorporated by reference), Daxx (J Biol Chem. 2006; 281:12664-72, hereby incorporated by reference), Gli (Dev Cell. 2006; 10: 719-29, hereby incorporated by reference), AWP-1, cullin-4B, cullin-7 (Oncogene 2011; 30:4350-64), and DEK.

The invention also provides a kit, comprising: at least one unit dosage form of a pharmaceutical composition comprising a therapeutically effective amount of lestaurtinib or a pharmaceutically effective salt thereof; and instructions for carrying out any method disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-2C depict cell growth suppression by lestaurtinib and its homologue staurosporine (STS) in 3 prostate cancer cell lines: PC3 (FIG. 2A), 22RV1 (FIG. 2B), and LNCaP clone FGC (FIG. 2C).

FIG. 3A-3C depictcell growth suppression by lestaurtinib and its homologue staurosporine (STS) in 3 breast cancer cell lines: MCF7 (FIG. 3A), BT-474 (FIG. 3B), and ZR-75-1 (FIG. 3C).

FIG. 4A-4D depict cell growth suppression by lestaurtinib and its homologue staurosporine (STS) in 4 gastric cancer cell lines: AGS (FIG. 4A), MKN-45 (FIG. 4B), Hs746T (FIG. 4C), and NCI-N87 (FIG. 4D).

FIG. 5 depicts a summary table for the $IC_{50}$ of lestaurtinib in all the tested cancer cell lines.

FIG. 8A-8C depict the dose-response impact of lestaurtinib on SRC3 (FIGS. 8A and 8B) and DEK (FIGS. 8A and 8C) protein expression levels in two prostate cancer cells.

FIG. 9A-9C depict the dose-response impact of lestaurtinib on SRC3 (FIGS. 9A and 9B) and DEK (FIGS. 9A and 9C) protein expression levels in two breast cancer cells.

FIG. 10A-10C depict the dose-response impact of lestaurtinib on SRC3 (FIGS. 10A and 10B) and DEK (FIGS. 10A and 10C) protein expression levels in two gastric cancer cells.

FIG. 11 depicts the amino acid sequence of human SPOP (SEQ ID NO: 15).

DETAILED DESCRIPTION OF THE INVENTION

Figure 1:
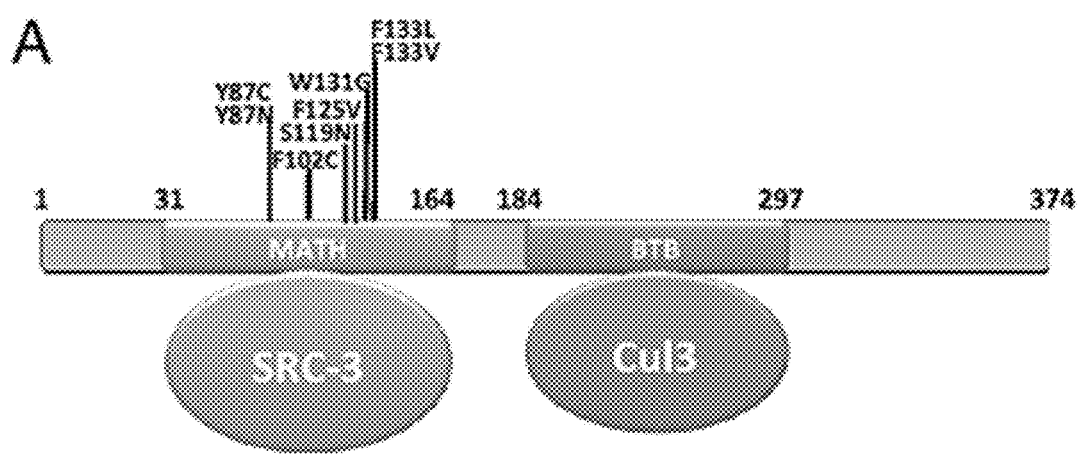
FIG. 1 depicts the structure of SPOP protein and sites of exemplary SPOP mutations.

General Techniques:

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Sambrook, Fritsch and Maniatis, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), and ANIMAL CELL CULTURE (R. I. Freshney, ed. (1987), which are hereby incorporated by reference).

As used in the specification and claims, the singular forms "a", "an" and "the" include plural references unless the context clearly dictates otherwise. For example, the term "a cell" includes a plurality of cells, including mixtures thereof.

Definitions

The terms "polypeptide", "peptide", and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "amino acid", as used herein, encompasses naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., γ-carboxyglutamate, hydroxyproline, and O-phosphoserine. Amino acid analogs refers to compounds that have the same basic chemical structure as a naturally occurring amino acid, i.e., an a carbon that is bound to a hydrogen, a carboxyl group, an amino group, and an R group. Exemplary amino acid analogs include but are not limited to homoserine, norleucine, methionine sulfoxide, and methionine methyl sulfonium. Such analogs can have modified R groups (e.g., norleucine) or modified peptide backbones, as long as they retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission.

In the context of polypeptides, a "sequence" is an order of amino acids in a polypeptide in an amino to carboxyl terminus direction in which residues that neighbor each other in the sequence are contiguous in the primary structure of the polypeptide.

The terms "polynucleotides", "nucleic acid", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed into mRNA, and/or the process by which the transcribed mRNA (also referred to as "transcript") is subsequently being translated into peptides, polypeptides, or proteins. The transcripts and/or the encoded polypeptides can be assessed as a readout for expression level. If the polynucleotide is derived from genomic DNA, expression may include splicing of the mRNA in a eukaryotic cell.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

A "sub-therapeutic amount" can be an amount less than the effective amount for that agent. When combined with an effective or sub-therapeutic amount of one or more additional agents, the sub-therapeutic amount can produce a result desired by the physician, due to, for example, synergy in the resulting efficacious effects, or reduced adverse effects.

As used herein, the terms "treatment" or "treating" are used interchangeably herein. These terms refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. For prophylactic benefit, the compositions may be administered to a subject at risk of developing a particular disease, or to a subject reporting one or more of the physiological symptoms of a disease, even though a diagnosis of this disease may not have been made.

The term "co-administration," "administered in combination with," and their grammatical equivalents, as used herein, encompass administration of two or more agents to an animal so that both agents and/or their metabolites are present in the subject at the same time. Co-administration includes simultaneous administration in separate compositions, administration at different times in separate compositions, or administration in a composition in which both agents are present.

The term "pharmaceutically acceptable salt" refers to salts derived from a variety of organic and inorganic counter ions well known in the art and include, by way of example only, base addition salts and acid addition salts. Base addition salts can be formed in cases wherein the compound comprises an acidic moiety. Acid addition salts can be formed in cases wherein the compound comprises a basic moiety. Exemplary base addition salts include alkali metal salts such as, e.g., sodium, potassium, and lithium salts, alkaline earth metal salts such as, e.g., calcium and magnesium salts, ammonium salts such as ammonium and tetraalkylammonium salts, salts with organic bases such as triethylamine, morpholine, piperidine and dicyclohexylamine; and salts with basic amino acids such as arginine and lysine. Exemplary acid addition salts can include, salts of organic or inorganic acids, such as hydrochloride, hydrobromide, sulfate, nitrate, formate, acetate, benzoate, maleate, fumarate, succinate, tartrate, citrate, oxalate, methanesulfonate, toluenesulfonate, aspartate, glutamate, and the like. In a compound with more than one basic moiety, more than one of the basic moieties may be converted to the salt form, including but not limited to a bis- or tris-salt. Alternatively, a compound having more than one basic moiety may form a salt at only one of the basic moieties. Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

The term "halogen" or "halo" as used herein denotes fluorine, chlorine, bromine, or iodine.

The terms "signaling", "signaling pathway", "pathway activity", and "signaling pathway activity" are used interchangeably herein to refer to a process during which signals are transmitted into, out of, and/or within a cell to elicit an intracellular response. The term "SPOP substrate signaling" generally refers to one or more signaling pathways mediated by an SPOP substrate. Exemplary SPOP substrates and SPOP substrate signaling pathways are described herein. The term "SPOP substrate signaling" encompasses protein/protein, protein/glycoprotein, protein/nucleic acid, and/or nucleic acid/nucleic acid interactions mediated by an SPOP substrate and/or one or more downstream molecules mapped to an SPOP substrate pathway. Non-limiting examples of such downstream molecules are described herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

Overview

The methods, compositions, and kits of the invention are related to the discovery that lestaurtinib can reduce expression levels and/or pathway activity of an SPOP substrate or that of its downstream target. Accordingly, described herein are methods of downregulating SPOP substrate signaling in a subject in need thereof. Aberrantly high levels and/or pathway activity of certain SPOP substrates have been implicated in a number of diseases, e.g., certain types of cancer. For example, aberrantly high levels and/or pathway activity of certain SPOP substrates are associated with tumors, e.g., prostate, breast or gastric cancer. Accordingly, disclosed herein are a number of methods and compositions for the use of lestaurtinib in the treatment of prostate, breast or gastric tumors in subjects comprising aberrantly high levels of one or more SPOP substrates or their signaling pathway activities. Any of the methods can comprise administering to the subject a pharmaceutical composition comprising a therapeutically effective amount of lestaurtinib or pharmaceutically acceptable salt thereof. Also described herein is a method of downregulating one or more SPOP substrates or signaling pathway activities thereof in a prostate, breast or gastric cell. The method may comprise (a) administering to the cell an effective amount of lestaurtinib or pharmaceutically acceptable salt thereof, thereby downregulating the one or more SPOP substrates or signaling pathway activities thereof in the tumor cell such as prostate, breast or gastric cancer, and (b) assessing downregulation of the one or more SPOP substrates or signaling pathway activities thereof in the tumor cell such as prostate, breast or gastric cancer. The methods, compositions, and kits of the invention are further related to the finding that lestaurtinib-mediated downregulation of an SPOP substrate and SPOP substrate pathway activity correlates with the ability of lestaurtinib to reduce viability of tumor cells.

Accordingly, further disclosed herein is a method of treating a tumor in a subject in need thereof. The method may comprise (a) administering to the subject a first dose of a pharmaceutical composition comprising a therapeutically effective amount of lestaurtinib or pharmaceutically acceptable salt thereof; (b) determining an SPOP substrate level or its activity in a biological sample derived from the subject; and (c) administering an additional dose of the pharmaceutical composition if the substrate level or its activity is reduced as compared to a control subject that is not administered a pharmaceutical composition comprising a therapeutically effective amount of lestaurtinib or pharmaceutically acceptable salt thereof. Also disclosed herein are kits for practicing any of the methods of the invention.

Exemplary SPOP Substrates and SPOP Substrate Signaling Pathways

In practicing any of the methods of the invention, the SPOP substrate to be downregulated can be any protein capable of forming a complex with SPOP. In some embodiments, the SPOP substrate to be downregulated is a protein which is capable of forming a complex with wild-type SPOP. Formation of a complex with SPOP (e.g., with wild-type SPOP) can be evidenced by binding of the substrate with SPOP. The binding can be a weak or strong binding. The binding can involve transient or permanent binding. In some embodiments, the SPOP substrate is capable of forming a complex with SPOP via one or more amino acids in a MATH domain of SPOP protein. The MATH domain may comprise amino acids 31-161 of the SPOP amino acid sequence. In some embodiments, the SPOP substrate is capable of forming a complex with one or more amino acids between and including amino acid positions 31-161 of the SPOP protein sequence. In some embodiments, the SPOP substrate is capable of forming a complex with one or more amino acids between and including amino acid positions 60-140 of the SPOP protein sequence. In some embodiments, the SPOP substrate is capable of forming a complex with one or more amino acids between and including amino acid positions 87-133 of the SPOP protein sequence. In some embodiments, the SPOP substrate is capable of forming a complex with a fragment of SPOP protein. The fragment may comprise a portion or all of a MATH domain of the SPOP amino acid sequence. For example, the fragment may comprise amino acids 31-161, 60-140, or 87-133 of the SPOP protein sequence.

SPOP substrates which can form a complex with SPOP can include proteins comprising an SPOP consensus binding sequence (SPOP-CBS). The SPOP-CBS can comprise the sequence S-S/T-S/T. The SPOP-CBS can comprise the sequence $\pi$-S-S/T-S/T or $\varphi$-$\pi$-S-S/T-S/T, wherein $\varphi$ is a non-polar amino acid and $\pi$ is a polar amino acid. Exemplary non-polar amino acids include, but are not necessarily limited to A, C, G, I, L, M, F, P, W, Y, and Z. Exemplary polar amino acids include, but are not necessarily limited to R, N, D, Q, Z, and K. The SPOP-CBS can comprise the sequence S-S/T-S/T preceded by an acidic amino acid (e.g., D or Z). For example, the SPOP-CBS can comprise the sequence D/E-$X_i$-S-S/T-S/T, wherein X is any amino acid and $_i$=0-2. In some embodiments, $_i$=0. In some embodiments, $_i$=1. In some embodiments, $_i$=2. In some embodiments, the SPOP-CBS is DSTT (SEQ ID NO: 1), DVSST (SEQ ID NO: 2), EVTSTT (SEQ ID NO: 3), or DSTSS (SEQ ID NO: 4). Polypeptides comprising an SPOP-CBS can be identified by searching a protein database for polypeptides containing the SPOP-CBS sequence. For example, an SPOP-CBS sequence can be used to query protein sequences using the protein BLAST algorithm. Exemplary SPOP substrates comprising an SPOP-CBS include, by way of example only, AWP1, Linker for activation of T-cells family member 1, cullin 4B, and cullin 7.

The capability of an SPOP substrate to form a complex with SPOP or fragment thereof can be determined by any means known to those of skill in the art. For example, numerous methods for assessing protein-protein interactions are available to a skilled artisan. In some embodiments, formation of the complex is detected by a binding assay. The binding assay can be used to detect binding between SPOP and a protein suspected to be an SPOP substrate. Exemplary binding assays include, but are not limited to co-immunoprecipitation, pull-down assays, cross-linking protein interaction analysis, Label Transfer Protein Interaction Analysis, and far-western blot analysis. Other assays for detecting protein-protein interactions include, e.g., yeast two hybrid assays, and surface plasmon resonance assays.

Co-immunoprecipitation assays typically involve the use of a capturing antibody to capture a target protein and any other proteins complexed with the target protein. The proteins that are complexed with the target can then be assayed by any means known in the art, such as, e.g., Coomassie staining, antibody detection, and/or label detection. By way of example only, a protein sample comprising a suspected SPOP substrate can be incubated with an SPOP antibody immobilized on a solid or semi-solid support, e.g., a bead. Any complexes comprising SPOP (or SPOP fragment) and an SPOP binding partner (e.g., an SPOP substrate) can be captured by the immobilized SPOP antibody. The complexes can then be analyzed by any means known in the art to identify the SPOP binding partner.

Pull-down assays typically use a bait protein captured on a solid or semi-solid surface. The immobilized bait protein can then be incubated with a protein sample comprising potential "prey" proteins. "Prey" proteins may form a complex with the immobilized bait protein. Captured "prey" proteins may then be eluted and assessed by any means known in the art.

Chemical cross-linking can be used to "fix" protein interactions in place prior to isolation or identification of binding partners. Common crosslinkers for this application include the non-cleavable NHS-ester cross-linker, bissulfosuccinimidyl suberate (BS3); a cleavable version of BS3, dithiobis (sulfosuccinimidyl propionate) (DTSSP); and the imidoester cross-linker dimethyl dithiobispropionimidate (DTBP) that is popular for fixing interactions in ChIP assays. Following cross-linking, protein binding partners can be detected and/or identified by any means known to those of skill in the art. For example, a binding partner can be identified by mass spectrometry, e.g., high mass MALDI mass spectrometry.

Label transfer can be used for screening or confirmation of protein interactions and can provide information about the interface where the interaction takes place. In a typical label transfer reaction, a bait protein is linked to a detectable label. This labeled bait protein can then be allowed to form a complex with a prey protein. Upon complex formation, the link to the detectable label is transferred from the bait protein to the prey protein. The protein-protein interaction can then be analyzed by multiple methods, including Western blot analysis, protein sequence analysis and mass spectrometry.

In a far-Western analysis, a labeled or antibody-detectable "bait" protein is generally used to probe and detect a target "prey" protein on the membrane. Proteins in a sample containing the prey protein are separated by sodium dodecyl sulfate-polyacrylamide gel electrophoresis (SDS-PAGE) or native PAGE and then immobilized on a solid or semi-solid support. After transfer, the solid or semi-solid support is probed with a labeled bait protein. The bait protein is allowed to form a complex with an immobilized binding partner. A detection system, dependent upon the label used, identifies the band that corresponds to the binding partner.

A yeast two hybrid assay is premised on the finding that a transcription factor for activating expression of, e.g., a reporter gene, can be divided into two modular components. The modular components can include a DNA binding component and a transcription activating component. In a yeast two hybrid assay, a yeast strain is transfected with "bait" and "prey" plasmids. The bait plasmid generally encodes a "bait" protein fused with one of the two modular components (e.g., the DNA binding component), while the "prey" plasmid generally encodes a suspected binding partner of the "bait" protein fused with the other of the two modular components (e.g., the transcription activating component). Formation of a complex comprising the "bait" protein and binding partner generally brings the two components of the transcription factor in sufficient proximity to effect transcription of the reporter gene. Detection of activated reporter gene transcription can indicate formation of a complex between the bait protein and binding partner. In some embodiments, the bait protein is SPOP or SPOP fragment and the binding partner is a suspected SPOP substrate. In some embodiments, the bait protein is a suspected SPOP substrate and the binding partner is SPOP or SPOP fragment.

Surface Plasmon Resonance (SPR) can also be used to detect SPOP binding partners. SPR typically utilizes a bait protein immobilized onto an SPR crystal. A liquid solution comprising "prey" proteins is injected over the bait layer. Formation of a complex between bait and prey is evidenced by an increase in SPR signal (expressed in response units, RU).

In some embodiments, the SPOP substrate to be downregulated is a protein capable of being ubiquitinated by a SPOP/ubiquitin ligase complex. The capability of an SPOP substrate to be ubiquitinated by SPOP/ubiquitin ligase complex can be determined in vivo or in vitro by methods described herein or otherwise known in the art. For example, ubiquitination of an SPOP substrate by a SPOP/ubiquitin ligase complex can be determined in vitro. An exemplary in vitro ubiquitination assay comprises combining in solution (1) the suspected SPOP substrate, (2) ubiquitin, (3) SPOP/ubiquitin ligase, and (4) any reaction components required for ubiquitination. The solution can be incubated for a time sufficient for ubiquitination of an SPOP substrate to occur.

Ubiquitination of an SPOP substrate by a SPOP/ubiquitin ligase complex can be determined in vivo. By way of example only, cultured cells can be transfected with tagged ubiquitin, the suspected SPOP substrate, and/or SPOP. The cells can be treated with a proteosomal inhibitor to enable accumulation of ubiquitinated proteins. Ubiquitinated proteins comprising the tagged ubiquitin can be immobilized onto a solid or semi-solid support, and detected and/or identified by any means known in the art, such as, e.g., immunoassay.

SPOP substrates can include proteins which are degraded by an SPOP/ubiquitin ligase complex. SPOP-mediated degradation of an SPOP substrate can be determined in vivo or in vitro. SPOP-mediated degradation of an SPOP substrate can be determined in vivo by, for example, incubating cells expressing an SPOP substrate in the presence or absence of SPOP, and comparing the levels of SPOP substrate in cells grown in the presence of SPOP to the levels of SPOP substrate in cells grown in the absence of SPOP. A reduction in the level of SPOP substrate in cells grown in the presence of SPOP as compared to SPOP substrate levels in cells grown in the absence of SPOP can be indicative of SPOP-mediated degradation of the SPOP substrate.

In some embodiments, the SPOP substrate pathway activity to be downregulated is an androgen signaling pathway in the subject. In some cases, the SPOP substrate to be downregulated enhances activity of an androgen signaling pathway. Androgen signaling is generally mediated by the androgen receptor. Binding of an androgen hormone ligand to AR generally induces nuclear translocation of the AR. AR can then recruit coregulatory proteins which can modulate AR-mediated transcriptional regulation of target genes. For example, activated AR can bind to an AR response element and activate transcription of an AR target gene. Exemplary AR target genes include, but are not limited to TMPRSS2, IGF1-R, NKXX3.1, CXCR4, MAK, MAF, N4A1, GREB1, and FKBP5. Such AR target genes represent non-limiting examples of downstream molecules mapped to an SPOP substrate pathway.

In some embodiments, the SPOP substrate that enhances androgen receptor signaling is an AR coregulatory protein, which also enhances Estrogen Receptor (ER) signaling. Exemplary AR and ER coregulatory proteins which are SPOP substrates include the p160 coactivator family proteins. P160 coactivator proteins can include SRC1, SRC2 (TIF2), and SRC3 (also known as $AIB_1$). These p160 coactivator proteins can activate AR/ER-mediated transcriptional activation of AR/ER target genes. In particular, SRC3 can significantly activate AR/ER-mediated transcription of target genes, and can be ubiquitinated by an SPOP/E3 ubiquitin ligase complex. Accordingly, in some embodiments, the method involves downregulating p160 coactivator protein signaling pathway in a subject in need thereof. In some embodiments, the p160 coactivator protein is SRC3. Without wishing to be bound by theory, it is possible that reduced SPOP activity can result in reduced ubiquitination of SRC3, thereby increasing SRC3 protein levels and subsequently increasing AR-specific gene expression. Accordingly, in some embodiments, an invention method comprises downregulating SRC3 level or its signaling activity in a subject in need thereof.

SPOP substrates which affect androgen signaling can also include, e.g., AN1-type zinc finger protein 6 (AWP1). AWP1 generally refers to a zinc finger protein that interacts with tumor necrosis factor receptor-associated factor 2 (TRAF2) (Int J Biochem Cell Biol 2011; 43: 1612-1620). Reducing AWP1 protein level can increase tumor necrosis factor alpha (TNFα)-induced cell death (Int J Biochem Cell Biol 2011; 43: 1612-1620). By contrast, increasing AWP1 protein can inhibit cell death, thereby enhancing tumor formation. AWP1 also interacts with PRK1, a Protein kinase C family serine/threonine kinase (Gene 2000; 256: 113-121). Stimulation of PRK1 can cause ligand-dependent superactivation of AR (EMBO J 2003; 22: 270-280). Without wishing to be bound by theory, it is possible that reduced SPOP activity can result in reduced ubiquitination of AWP1, thereby increasing AWP1 protein levels and AWP1 activity. AWP1 pathway activity can reduce cell death of, e.g., prostate tumor cells. Furthermore, AWP1 pathway activity can enhance PRK1 signaling and subsequently induce AR superactivation. Accordingly, in some embodiments, an invention method comprises downregulating AWP1 or AWP1 signaling in a subject in need thereof.

SPOP substrates which affect androgen signaling can also include Gli proteins. Gli proteins generally refer to a class of protein transcription factors which mediate the hedgehog signaling pathway. Gli proteins can include Gli1, Gli2, and Gli3. In particular, Gli1 can act in humans as an oncoprotein. Gli pathway activity can enhance AR-specific gene expression and can enable androgen-sensitive LNCaP cells to grow in androgen-depleted medium. Without wishing to be bound by theory, it is possible that reduced SPOP activity can result in reduced ubiquitination of Gli, thereby increasing Gli protein levels and subsequently increasing AR-specific gene expression. Accordingly, in some embodiments, the method involves downregulating Gli substrate signaling in a subject in need thereof. In particular embodiments, the Gli substrate signaling pathway is a Gli1 substrate signaling pathway.

SPOP substrates can potentially include DEK; its protein sequence has the presence of DSSTT (SEQ ID NO: 5) and DESSS (SEQ ID NO: 6) consensus motif, suggesting that DEK could possibly be degraded by SPOP mediated pathway, and levels increased if SPOP has loss-of-function mutations or loss of protein expression for other reasons. In both prostate and gastric cancer cells, the expression levels of DEK appeared to be higher than SRC3, whereas in breast cancer DEK expression level was lower but showed a decrease after breast cancer cells were treated with lestaurtinib, which is similar to SRC3.

In some embodiments, the SPOP substrate or substrate pathway activity to be downregulated affects cell proliferation, survival, and/or apoptosis. For instance, a SPOP substrate can repress apoptosis in a cell. Downregulation of signaling activity of such SPOP substrates can possibly enhance apoptosis of a tumor cell, e.g. a prostate tumor cell. Exemplary SPOP substrates that repress cellular apoptosis include, but are not limited to AWP1 and Daxx. Daxx pathway activity can repress cell death. For example, Daxx pathway activity can inhibit cell death by inhibiting activity of the tumor suppressor p53. Without wishing to be bound by theory, it is possible that reduced SPOP activity can result in reduced ubiquitination of Daxx, thereby increasing Daxx protein levels and subsequently repressing cell death of, e.g., a tumor cell. Accordingly, in some embodiments, the method involves downregulating Daxx substrate signaling in a subject in need thereof.

Downregulation of SPOP Substrate Level or Activity

In practicing any of the methods of the invention, administration of a pharmaceutical composition comprising a therapeutically effective amount of lestaurtinib to a subject in need thereof can result in downregulation of an SPOP substrate level and/or pathway activity in the subject. Likewise, administration of an effective amount of lestaurtinib to a tumor cell can result in an SPOP substrate level and/or pathway activity in the tumor cell. Exemplary SPOP substrates, and pathway activities thereof, are described herein. Downregulation of SPOP substrate levels and/or pathway activities thereof can be determined by a variety of methods described herein or otherwise known in the art. For example, downregulation of SPOP substrate levels and/or its pathway activities in a subject can be determined by comparison to a control subject and/or control population. The SPOP substrate and/or its signaling can be considered downregulated in the subject if the level of the substrate or signaling in the subject is reduced as compared to a control subject and/or control population. The control subject can be an individual that has not been administered lestaurtinib. Likewise, a control population can encompass a plurality of individuals that have not been administered lestaurtinib. The control subject can be a subject in need of SPOP substrate downregulation or downregulation of SPOP substrate activity, that is not administered lestaurtinib. The SPOP substrate or pathway activity thereof may be reduced as compared to a control subject in need thereof but was not administered lestaurtinib.

The control subject does not have to be a different individual from said subject, but may be the same subject at an earlier time point, e.g., the same subject prior to receiving a first dose of lestaurtinib. Accordingly, downregulation of an SPOP substrate or its signaling in the subject following first administration of lestaurtinib may be compared to an SPOP substrate level or pathway activity thereof in the same subject prior to first administration of lestaurtinib. For example, a method of assessing SPOP downregulation in a subject in need thereof can comprise measuring an SPOP substrate level or is pathway activity in the subject or in a biological sample derived from the subject at a first time point. The subject may have, be suspected of having, or be suspected of being at increased risk for any of the diseases described herein. The subject may, for example, have a prostate, breast or gastric tumor. The first time point may be a time point prior to administration of a composition as described herein. The method may further comprise measuring the SPOP substrate level or pathway activity thereof in the subject or in a biological sample derived from the subject at a second time point. The second time point may follow administration of the composition. The level measured at the second time point may be compared to the level measured at the first time point to determine whether downregulation has occurred. In some embodiments, downregulation indicates clinical efficacy of administration of the pharmaceutical composition. In some embodiments, the method further comprises administering an additional dose of the pharmaceutical composition if the level of the SPOP substrate or its pathway activity is reduced.

SPOP substrate level or its signaling may be determined in the subject or in a biological sample derived from the subject. The biological sample can be a fluid sample. Exemplary fluid samples include, e.g., whole blood, plasma, serum, ascites, cerebrospinal fluid, sweat, urine, tears, saliva, or buccal sample. The biological sample can also be a solid biological sample. Exemplary solid biological samples include, e.g., feces or a tissue biopsy. The biological sample can harbor or be suspected of harboring diseased cells or diseased tissue. The diseased cells or tissue can be tumor cells or tumor tissue. The tumor cells or tissue can be cancer cells or tissue. The cells can be, e.g., cancer stem cells or circulating tumor cells. The biological sample can harbor or be suspected of harboring macromolecules derived from diseased cells or tissue. The biological sample can be an essentially cell-free sample harboring or suspected of harboring macromolecules derived from diseased cells or tissue. The macromolecules can be polypeptides and/or polynucleotides. The polynucleotides can be, e.g., RNA or DNA.

An SPOP substrate level can refer to an SPOP substrate expression level. An SPOP substrate expression level can refer to a protein level and/or concentration of the SPOP substrate in a subject or biological sample. Protein levels and/or concentration can be determined by any means known in the art. Exemplary methods include, but are not limited to western blot, ELISA, immunoprecipitation, radioimmunoassay, mass spectrometry, imaging, e.g., PET imaging, immunofluorescence, protein microarray, and immunohistochemistry.

An SPOP substrate level can refer to a level and/or concentration of polynucleotide encoding the SPOP substrate protein. The polynucleotide can be, e.g., DNA and/or RNA. Methods of assessing levels and/or concentration of polynucleotides are known to those of skill in the art. Exemplary methods include, but are not limited to sequencing, next generation sequencing, microarray, polymerase chain reaction (PCR), real-time PCR (RT-PCR), digital PCR, in situ hybridization (ISH), RNase protection assay, and the like.

An SPOP substrate level can be evidenced by a level to which an SPOP substrate is targeted for degradation by, e.g., the ubiquitin-proteosome degradation pathway. Such demonstration can include, but is not limited to, evidence of SPOP substrate ubiquitination. Exemplary methods for assessing SPOP substrate ubiquitination are described herein. For example, enhanced ubiquitination of an SPOP substrate can indicate enhanced downregulation of the SPOP substrate. SPOP substrate level can be evidenced by assessing SPOP-mediated degradation of the SPOP substrate. Exemplary methods for assessing SPOP-mediated degradation of the SPOP substrate are described herein.

Level of SPOP substrate signaling in a subject or biological sample derived from the subject can be determined by any methods known to those of skill in the art and/or by methods described herein. Exemplary SPOP signaling pathways are described herein and include, e.g., androgen receptor signaling, PRK1 activity, and inhibition of cell death. Androgen receptor signaling can be determined in various ways. For example, androgen receptor signaling can be determined by measuring the level and/or concentration of androgen-receptor activated transcripts. Level and/or concentration of transcripts (e.g., mRNA transcripts) can be determined by methods described herein, e.g., RT-PCR, RNase protection assay, in situ hybridization, and the like. Androgen-receptor activated genes include, but are not limited to TMPRSS2, IGF1-R, NKXX3.1, CXCR4, MAK, MAF, N4A1, GREB1, and FKBP5. By way of other example, androgen receptor signaling can be determined by androgen receptor reporter assay. In an exemplary androgen receptor reporter assay, cells are transfected with a plasmid that expresses a reporter gene under control of an Androgen Receptor Response Element. Androgen Receptor activity can be inferred by the level of the detected reporter in the assay. Androgen receptor signaling can be determined by assessing sensitivity of the subject or biological sample derived from the subject to androgen. Sensitivity to androgen can be determined, e.g., by a dose-response curve, or by measuring the response of the subject or biological sample to known quantities of androgen.

PRK1 activity can be determined by methods described herein or otherwise known in the art. For example, PRK1 activity can be determined by assessing phosphorylation of known PRK1 targets. Known PRK1 targets include, e.g., Histone H3. PRK1 can phosphorylate Histone H3 at its Threonine 11 position (H3T11). PRK1-mediated H3T11 phosphorylation can result in enhanced androgen receptor signaling. H3T11 phosphorylation can be determined by, e.g., western blotting and/or kinase assay.

Another exemplary SPOP signaling pathway involves AWP1-mediated inhibition of TNFα-induced cell death. A TNFα signaling pathway can comprise activation of NF-κB. Activation of NF-κB can comprise recruitment of proteins TRAF2 and RIP. TRAF2 in turn can recruit the multicomponent protein kinase IKK, enabling the serine-threonine kinase RIP to activate it. An inhibitory protein, IκBα, that normally binds to NF-κB and inhibits its translocation, can be phosphorylated by IKK and subsequently degraded, releasing NF-κB. NF-κB generally refers to a heterodimeric transcription factor that translocates to the nucleus and mediates the transcription of a vast array of proteins involved in cell survival and proliferation, inflammatory response, and anti-apoptotic factors. A TNFα signaling pathway can comprise activation of MAPK pathways. For example, TNFα signaling can induce the stress-related JNK pathway, can induce the p38-MAPK pathway, and may also induce ERK. Recruited TRAF2/Rac can activate the JNKinducing upstream kinases of MLK2/MLK3, TAK1, MEKK1 and ASK1 (either directly or through GCKs and Trx, respectively). SRC-Vav-Rac axis can activate MLK2/MLK3. MLK2/MLK3 kinases can phosphorylate MKK7, which can then activate JNK. JNK can translocate to the nucleus and activates transcription factors such as c-Jun and ATF2. The JNK pathway can be a pro-apoptotic pathway. TNFα can also induce cellular necrosis. Cellular necrosis can be a caspase-independent cell death. TNFα-induced necrosis can be associated with generation of reactive oxygen species (ROS). ROS can be assessed by any means known in the art. For example, ROS can be assessed by a reporter probe that fluoresces upon oxidation. Exemplary probes that fluoresces upon oxidation includes 7'-dichlorofluorescein (DCF), carboxy-H2DCFDA, H2DFFDA, Dihydrocalcein, AM, aminophenyl fluorescein, hydroxyphenyl fluorescein, and calcein, among others. Kits for assessing ROS are commercially available from, e.g., Abcam, Cell Bio Labs, Life Technologies, and Sigma-Aldrich. Necrosis can also be determined by morphological analysis. Morphological hallmarks of necrosis include, but are not limited to dense clumping and progressive disruption of genetic material, and disruption to membranes of cells and organelles. For example, nuclear chromatin may fade due to DNA degradation. Necrosis may be evidenced by shrinkage of the nucleus, by chromatin condensation, and nuclear fragmentation. Plasma membranes may appear discontinuous. This discontinuous membrane may be caused by cell blebbing and the loss of microvilli. Cell death can be assessed by any means known in the art, including, but not limited to cell counting, MTT assay, TUNEL staining, Annexin V staining, Annexin V/Propidium iodide staining, and the like.

An exemplary invention method can comprise administration of an effective amount of lestaurtinib to a tumor cell, thereby downregulating an SPOP substrate level or its activity in the cell. The method can further comprise assessing downregulation of an SPOP substrate level or its activity in the tumor cell. Methods of assessing downregulation are described herein. The tumor cell can comprise an elevated level or pathway activity of an SPOP substrate. The tumor cell can be a cell derived from a subject as described herein. The tumor cell can be a prostate, breast or gastric tumor cell. The tumor cell can be an androgen- or estrogen-sensitive prostate, breast or gastric tumor cell. The tumor cell can be a cultured cell. The cultured cell can be, e.g., an LNCaP, PC3 or MCF7 cell. In some embodiments, the effective amount is 0.01 nM, 0.05 nM, 0.1 nM, 0.5 nM, 1 nM, 5 nM, 10 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1000 nM, 1100 nM, 1200 nM, 1300 nM, 1400 nM, 1500 nM, 1600 nM, 1700 nM, 1800 nM, 1900 nM, 2000 nM, 2100 nM, 2200 nM, 2300 nM, 2400 nM, 2500 nM, 2600 nM, 2700 nM, 2800 nM, 2900 nM, 3000 nM, 3100 nM, 3200 nM, 3300 nM, 3400 nM, 3500 nM, 3600 nM, 3700 nM, 3800 nM, 3900 nM, 4000 nM, 5000 nM, 6000 nM, 7000 nM, 8000 nM, 9000 nM, 10000 nM (10 µM), 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 200 µM, 300 µM, 400 µM, 500 µM, 600 µM, 700 µM, 800 µM, 900 µM, or 1000 µM (1 mM). In some embodiments, the effective amount is 0.01-10 nM, 10 nM-100 nM, 30 nM-1000 nM, 100 nM-3000 nM, 500 nM-10,000 nM (10 µM), 1-100 µM, or 50 µM-1000 µM (1 mM).

Administration of an effective amount of lestaurtinib or administration of a pharmaceutical composition comprising lestaurtinib may downregulate an SPOP substrate level or its pathway activity by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. Administration of a pharmaceutical composition described herein may downregulate SPOP substrate level or its pathway activity by 5-20%, 10-40%, 30-60%, 40-80%, 60-95%, or 75-99%.

Downregulation of an SPOP substrate level or its pathway activity by administration of a pharmaceutical composition comprising lestaurtinib can have a therapeutic benefit to the subject. For example, in cases wherein the subject is suffering from a tumor or cancer (e.g., a prostate tumor or cancer), downregulation of an SPOP substrate level or its pathway activity in the subject can reduce viability of a prostate tumor or cancer cell in the subject. Downregulation of an SPOP substrate level or its pathway activity can delay or halt progression of tumor or cancer cell growth in the subject, can reduce the number of cancer cells in the subject, can shrink a tumor or cancer in the subject, can prevent or delay metastasis of a tumor or cancer in the subject, or can prophylactically prevent formation of a tumor or cancer in the subject. In subjects with prostate cancer, downregulation of an SPOP substrate level or its activity can reduce blood PSA levels in the subject.

Downregulation of an SPOP substrate level or its activity in a subject can be used as an indicator of the therapeutic efficacy of lestaurtinib in the subject. Therefore, an invention method may comprise (a) administering to the subject a first dose of a pharmaceutical composition comprising a therapeutically effective amount of lestaurtinib or pharmaceutically acceptable salt thereof; (b) determining an SPOP substrate level or its activity in a biological sample derived from the subject; and (c) administering an additional dose of the pharmaceutical composition if the substrate level or its activity is reduced as compared to a control subject that is not administered a pharmaceutical composition comprising a therapeutically effective amount of lestaurtinib or pharmaceutically acceptable salt thereof.

Exemplary Subjects

In practicing any of the methods of the invention, the subject can be any subject in need of downregulation of an SPOP substrate level or its pathway activity. Exemplary subjects are described herein.

The subject in need of downregulation of an SPOP substrate level or its pathway activity may harbor a cell or tissue comprising an elevated level or pathway activity of an SPOP substrate. The subject in need of downregulation of an SPOP substrate level or its pathway activity may harbor a cell or tissue comprising an elevated level or pathway activity of an SPOP substrate. The subject's cell or tissue comprising an elevated level or pathway activity of an SPOP substrate may be a diseased tissue or cell, such as, e.g., a tumor or cancerous tissue or cell. In some embodiments, the diseased cell or tissue comprises an elevated level or pathway activity of an SPOP substrate, as compared to a non-diseased tissue or cell.

The SPOP substrate and/or pathway activity thereof which is elevated may have any of the SPOP substrates or signaling described herein. In some embodiments, the SPOP substrate/and or pathway activity that is elevated is a p160 steroid activator, such as SRC1, SRC2, or SRC3. In some embodiments, the SPOP substrate and/or pathway activity thereof which is elevated is SRC3. The SPOP substrate or pathway activity thereof which is elevated may be AWP1. The SPOP substrate or pathway activity thereof which is elevated may be Gli. The SPOP substrate or pathway activity thereof which is elevated may be Gli-1, Gli-2, and/or Gli-3. An SPOP substrate signaling pathway which is elevated may result in increased PRK1 signaling and/or PRK1 expression.

The elevated level or pathway activity of the SPOP substrate may be determined in the subject or in a biological sample derived from the subject. Exemplary biological samples are described herein.

In some embodiments, the level or pathway activity of the SPOP substrate in the subject or biological sample derived from the subject is elevated as compared to a level or pathway activity of the SPOP substrate in a reference subject or reference biological sample. In some embodiments, the reference subject does not harbor or is not suspected of harboring a disease associated with elevated SPOP substrate levels. In some embodiments, the reference biological sample is derived from a non-diseased tissue of the subject in need of SPOP substrate downregulation. In some embodiments, the level or pathway activity of the SPOP substrate in the subject or biological sample derived from the subject is considered elevated if the level or pathway activity is higher than a threshold level or pathway activity of the SPOP substrate. The threshold level or pathway activity can be determined by those of skill in the art, for example, by taking into account a range or an average of SPOP substrate or substrate pathway activity levels found in a cohort of subjects that are not in need of SPOP downregulation.

In some embodiments, the level or pathway activity of the SPOP substrate in the subject or biological sample derived from the subject is 5-50% higher, 40-100% higher, 80-200% higher, 100-500% higher, 400-1000%, higher, or more than 1000% higher that a level or pathway activity of the SPOP substrate in a reference subject or reference biological sample. In some embodiments, the level or pathway activity of the SPOP substrate in the subject or biological sample derived from the subject is 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 250%, 300%, 400%, 500%, 600%, 700%, 800%, 900%, 1000%, or more than 1000% higher that a level or pathway activity of the SPOP substrate in a reference subject or reference biological sample.

The subject or biological sample derived from the subject can exhibit elevated SPOP substrate pathway activity. As described herein, the SPOP substrate pathway that is elevated can be an androgen receptor signaling pathway. Androgen receptor signaling can be determined in various ways, as described herein or otherwise known in the art.

In some embodiments, the SPOP substrate pathway that is elevated results in inhibition of cell death, e.g., AWP1-mediated inhibition of TNFα-induced pathways. Exemplary TNFα-induced pathways are described herein. Methods for assessing cell death are described herein.

In some embodiments, the subject in need of downregulation of an SPOP substrate level or its pathway activity, or a biological sample derived from the subject, exhibits one or more SPOP mutations. The one or more SPOP mutations can include a mutation in a polynucleotide (e.g., DNA or RNA) encoding an SPOP protein (e.g., an SPOP gene). The mutation can affect any portion of the SPOP gene. The one or more SPOP mutations can include a mutation in the SPOP protein. The one or more SPOP mutations can be a point mutation, an insertion, a deletion, an amplification, a translocation, an inversion, or loss of heterozygosity. In some embodiments, the mutation is a loss of function or a dominant negative mutation. The mutation can be a frameshift mutation. A frameshift mutation can disrupt the reading frame, resulting in a completely different translated protein as compared to the original sequence. The mutation can be a nonsense mutation. The nonsense mutation can result in a premature stop codon, thus encoding a truncated, and possibly nonfunctional protein product. The SPOP mutation can be a nonsense mutation, wherein a single nucleotide alteration causes an amino acid substitution in the translated protein. The mutation can cause an alteration in the MATH domain of the SPOP protein. The mutation can alter an amino acid sequence between positions 31-161 of the SPOP amino acid sequence. The mutation can cause a substitution at Y87, F102, S119, F125, K129, W131, F133, and/or K134 of the SPOP amino acid sequence. In some embodiments, the mutation causes a Y87C substitution, a Y87N substitution, an F102C substitution, an S119N substitution, an F125V substitution, a K129N substitution, a W131G substitution, an F133L substitution, an F133V substitution, or any combination of substitutions thereof. The mutation can reduce binding efficacy of an SPOP protein with an SPOP substrate. The mutation can reduce the ability of SPOP to facilitate ubiquitination of the SPOP substrate. The mutation can reduce degradation of the SPOP substrate.

Presence of an SPOP mutation can be determined by any means known in the art, including genotyping assays and sequencing methods. Sequencing methods can include next-generation sequencing, targeted sequencing, exome sequencing, whole genome sequencing, massively parallel sequencing, and the like. Several platforms for next generation sequencing are commercially available. Commercially available platforms include, e.g., platforms for sequencing-by-synthesis, ion semiconductor sequencing, pyrosequencing, reversible dye terminator sequencing, sequencing by ligation, single-molecule sequencing, sequencing by hybridization, and nanopore sequencing. Platforms for sequencing by synthesis are available from, e.g., Illumina, 454 Life Sciences, Helicos Biosciences, and Qiagen. Illumina platforms can include, e.g., Illumina's Solexa platform, Illumina's Genome Analyzer, and are described in Gudmundsson et al (Nat. Genet. 2009 41:1122-6), Out et al (Hum. Mutat. 2009 30:1703-12) and Turner (Nat. Methods 2009 6:315-6), U.S. Patent Application Pub nos. US20080160580 and US20080286795, U.S. Pat. Nos. 6,306,597, 7,115,400, and 7,232,656, which are hereby incorporated by reference. 454 Life Science platforms include, e.g., the GS Flex and GS Junior, and are described in U.S. Pat. No. 7,323,305, hereby incorporated by reference. Platforms from Helicos Biosciences include the True Single Molecule Sequencing platform. Platforms for ion semiconductor sequencing include, e.g., the Ion Torrent Personal Genome Machine (PGM) and are described in U.S. Pat. No. 7,948,015, hereby incorporated by reference. Platforms for pryosequencing include the GS Flex 454 system and are described in U.S. Pat. Nos. 7,211,390; 7,244,559; 7,264,929, which are hereby incorporated by reference. Platforms and methods for sequencing by ligation include, e.g., the SOLiD sequencing platform and are described in U.S. Pat. No. 5,750,341, hereby incorporated by reference. Platforms for single-molecule sequencing include the SMRT system from Pacific Bioscience and the Helicos True Single Molecule Sequencing platform. Nanopore sequencing methodologies are described in Soni GV and Meller A. Clin Chem 53: 1996-2001 [2007], hereby incorporated by reference. Nanopore sequencing DNA analysis techniques are being industrially developed by a number of companies, including Oxford Nanopore Technologies (Oxford, United Kingdom). Nanopore sequencing generally refers to a single-molecule sequencing technology whereby a single molecule of DNA is sequenced directly as it passes through a nanopore. A nanopore can be a small hole, of the order of 1 nanometer in diameter. Immersion of a nanopore in a conducting fluid and application of a potential (voltage) across can result in a slight electrical current due to conduction of ions through the nanopore. The amount of current which flows is sensitive to the size and shape of the nanopore and to occlusion by, e.g., a DNA molecule. As a DNA molecule passes through a nanopore, each nucleotide on the DNA molecule can obstruct the nanopore to a different degree, changing the magnitude of the current through the nanopore in different degrees. Thus, this change in the current as the DNA molecule passes through the nanopore represents a reading of the DNA sequence. While the automated Sanger method is considered as a 'first generation' technology, Sanger sequencing including the automated Sanger sequencing, can also be employed by the method of the invention.

Any of the subjects described herein may be suffering from, be diagnosed with, be suspected of having, or be suspected of being at risk for developing a disease associated with aberrantly high levels of an SPOP substrate. The subject may, for example, be diagnosed with, be suspected of having, or be suspected of being at risk for developing a disease associated with aberrantly high levels of SRC3. Exemplary diseases associated with aberrantly high levels of SRC3 include, but are not limited to, prostate cancer, breast cancer, gastric cancer, and pancreatic cancer.

Any of the subjects described herein can be an animal. The animal can be a vertebrate. Exemplary vertebrates include amphibians, birds, mammals, and reptiles. Exemplary mammals include, but are not limited to mice, rabbits, guinea pigs, cats, dogs, pigs, sheep, horses, cows, humans, and monkeys. Exemplary amphibians include, but are not limited to frogs, toads, salamanders, and newts. Exemplary reptiles include, but are not limited to lizards, snakes, and turtles. Exemplary birds include, but are not limited to chickens, waterfowl, finches, songbirds, hawks, falcons, and eagles. In some embodiments, the subject is an invertebrate, e.g., Caenorhabditis elegans or an insect such as, e.g., Drosophila melongaster.

Exemplary Compounds

Generally, the methods of the invention comprise administering to the subject a pharmaceutical composition comprising a therapeutically effective amount of a compound of Formula (I), or a pharmaceutically acceptable salt thereof. In some embodiments, an invention method comprises administering to a tumor cell an effective amount of a compound of Formula (I), or a pharmaceutically acceptable salt thereof. In some embodiments, a compound of Formula I is:

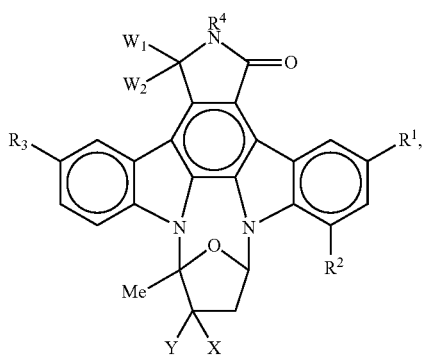

(I)

wherein $R^1$, $R^2$, $R^3$, and $R^4$ are independently H, acetyl, amido, a halogen, $CONH_2$, OH, $CH_2CH_2Br$, wherein $W^1$ and $W^2$ are independently H, O, $O_2$, wherein X is OH, CONHOH, $CONH_2$, $CONHCH_2CH_2OH$, $CO_2Et$, $CO_2Me$, $CH_2OH$, $CH_2OCOCH_2CH_2CO_2H$, $CH_2N_3$, $CH_2NH_2$, $CH_2NHCH_2CO_2Me$, $CH_2NHCH_2CO_2H$, $CH_2N$=CH-$NMe_2$, $CH_2NHCOCH_2NH_2$, —$CH_2O$—, $CH_2NHMe$, $CH_2NHCH_2CH$=$CH_2$, $CH_2NHCH_2CH(OH)CH_2O$, $CH_2SMe$, $CH_2S(O)Me$, —O—,

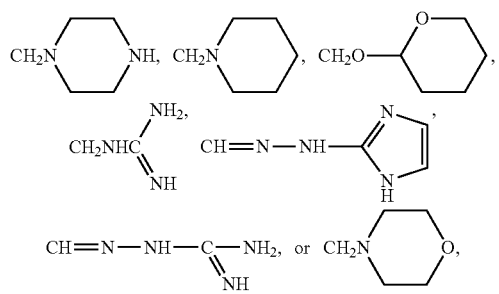

wherein Y is OH, O-acetyl, or X and Y together form a ring.

In some embodiments, at least one of $R^1$, $R^2$, $R^3$, and $R^4$ is H. In some embodiments, at least two of $R^1$, $R^2$, $R^3$, and $R^4$ are H. In some embodiments, at least three of $R^1$, $R^2$, $R^3$, and $R^4$ are H. In some embodiments, each of $R^1$, $R^2$, $R^3$, and $R^4$ is H. In some embodiments, at least one of $W^1$ and $W^2$ is H. In some embodiments, at least one of X or Y is OH. In some embodiments, X is CH2OH.

In some embodiments, each of $R^1$, $R^2$, $R^3$, and $R^4$ are H, $W^1$ and $W^2$ are H, X is $CH_2OH$, and Y is OH.

In some embodiments, the compound is a compound of Formula (II) or a pharmaceutically acceptable salt thereof:

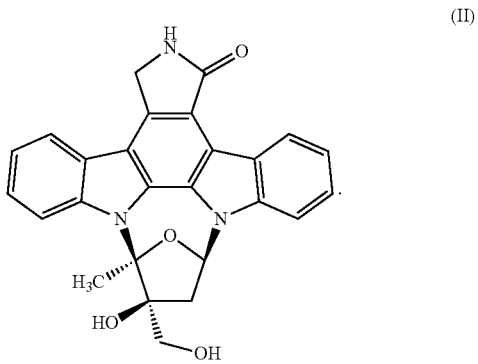 [SMILES: C[C@]12O[C@H](C[C@]1(O)CO)n1c3ccccc3c3c4c(c5c6ccccc6n2c5c31)CNC4=O]

(II)

Such compounds are generally referred to herein as "lestaurtinib", "CEP-701"; "KT-5555"; "SPM-924". Such compounds, and methods of making the compounds, are described in U.S. Pat. No. 4,923,986, PCT Publication Nos. WO2007075307, WO2008086510, all of which are hereby incorporated by reference. In general, lestaurtinib can be formulated as pharmaceutically acceptable free base or salt forms. Pharmaceutically acceptable salts are described herein.

Compounds of Formula I or Formula II (e.g., lestaurtinib) may be purchased through several vendors for the manufacture of the pharmaceutical composition. For example, lestaurtinib is listed in the CAS registry (CAS #111358-88-4). Lestaurtinib may be purchased from, e.g., Tocris Biosciences (catalog #3395), LC Laboratories (catalog #L-6307), Cayman Chemical (catalog #12094), BioVision, Inc. (Catalog #1805-1000), and Santa Cruz Biotech (catalog #sc-218657), among others. In some embodiments, compounds or pharmaceutical compositions comprising compounds of Formula I or Formula II may be manufactured by Cephalon, Inc. or Abbott Laboratories, Inc.

Pharmaceutical Compositions

In general, the methods of the invention utilize pharmaceutical compositions comprising a therapeutically effective amount of lestaurtinib. The compositions comprising an effective amount of a compound of Formula I or Formula II may include a pharmaceutically acceptable carrier. The pharmaceutically acceptable carrier for the present compositions may include, but are not limited to, amino acids, peptides, biological polymers, non-biological polymers, simple sugars or starches, inorganic salts, and gums, which may be present singly or in combinations thereof. The peptides used in the acceptable carrier may include, e.g., gelatin and/or albumin. Cellulose or its derivatives may be used in the pharmaceutically acceptable carrier. The sugar used in the acceptable carrier may be lactose and/or glucose. Other useful sugars which may be utilized in the pharmaceutical compositions include but are not limited to, fructose, galactose, lacticol, maltitol, maltose, mannitol, melezitose, myoinositol, palatinate, raffinose, stachyose, sucrose, tehalose, xylitol, hydrates thereof, and combinations of thereof. Binders may be included in the pharmaceutically acceptable carrier. Examples of binders include, but are not limited to, starches (for example, corn starch or potato starch), gelatin; natural or synthetic gums such as acacia, sodium alginate, powdered tragacanth, guar gum, cellulose or cellulose derivatives (for example, methycellulose, ethyl cellulose, cellulose acetate); microcrystalline cellulose, polyvinyl pyrrolidone, and mixtures thereof. Inorganic salts used in the acceptable carrier may be a magnesium salt, for example, magnesium chloride or magnesium sulfate. Other inorganic salts may be used, for example, calcium salts. Examples of calcium salts include, but are not limited to, calcium chloride, calcium sulfate. Other examples of substances which may be used in the pharmaceutically acceptable carrier include, but are not limited to, vegetable oils, such as peanut oil, cottonseed oil, olive oil, corn oil; polyols such as glycerin, propylene glycol, polyethylene glycol; pyrogen-free water, isotonic saline, phosphate buffer solutions; emulsifiers, such as the Tweens®; wetting agents, lubricants, coloring agents, flavoring agents, preservatives.

The term "wetting agents" may be used interchangeably with "surfactants", and refers to substances that lower the surface tension of a liquid, thus allowing the liquid to spread more easily. Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. A useful parameter that may be used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are generally considered to be compounds having an HLB value equal to or less than about 10. However, HLB value of a surfactant merely provides a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts, fatty acid derivatives of amino acids, glyceride derivatives of amino acids, fusidic acid salts, oligopeptides, and polypeptides, oligopeptides, and polypeptides, lecithins and hydrogenated lecithins, lysolecithins and hydrogenated lysolecithins, phospholipids and derivatives thereof, fatty acid salts, lysophospholipids and derivatives thereof, carnitine fatty acid ester salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Within the aforementioned group, ionic surfactants include, but are not limited to, lecithins, lysolecithin, phospholipids, lysophospholipids and derivatives thereof, carnitine fatty acid ester salts, fatty acid salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Ionic surfactants may be the ionized forms of lactylic esters of fatty acids, lecithin, lysolecithin, phosphatidylethanolamine, phosphatidylcholine, phosphatidylglycerol, phosphatidic acid, phosphatidylserine, lysophosphatidylcholine, lysophosphatidylserine, lysophosphatidylethanolamine, lysophosphatidylglycerol, lysophosphatidic acid, PEG-phosphatidylethanolamine, PVP-phosphatidylethanolamine, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, linoleate, linolenate, stearate, ricinoleate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides, alkylthioglucosides, alkylmaltosides, lauryl macrogolglycerides, polyoxyalkylene alkyl ethers such as polyethylene glycol alkyl ethers, polyoxyalkylene alkylphenols such as polyethylene glycol alkyl phenols, polyethylene glycol glycerol fatty acid esters, polyoxyalkylene alkyl phenol fatty acid esters such as polyethylene glycol fatty acids monoesters and polyethylene glycol fatty acids diesters, polyglycerol fatty acid esters, polyoxyethylene-polyoxypropylene block copolymers and mixtures thereof, polyoxyalkylene sorbitan fatty acid esters such as polyethylene glycol sorbitan fatty acid esters, hydrophilic transesterification products of a polyol with at least one member of the group consisting of glycerides, vegetable oils, hydrogenated vegetable oils, fatty acids, and sterols, polyoxyethylene sterols and derivatives or analogues thereof, polyoxyethylated vitamins and derivatives thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-12 oleate, PEG-15 oleate, PEG-20 oleate, PEG-20 laurate, PEG-32 dilaurate, PEG-32 laurate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-20 trioleate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-50 hydrogenated castor oil, PEG-40 castor oil, PEG-35 castor oil, PEG-60 castor oil, PEG-40 palm kernel oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, but are not limited to, fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar ethers, sugar esters, hydrophobic transesterification products of a polyol with at least one member of the group consisting of glycerides, vegetable oils, hydrogenated vegetable oils, fatty acids and sterols, oil-soluble vitamins/vitamin derivatives, lactic acid derivatives of mono- and di-glycerides, and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Lubricants that may be used in the pharmaceutical composition include, but are not limited to, agar, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, or mixtures thereof. Additional lubricants include, by way of example, a syloid silica gel, a coagulated aerosol of synthetic silica, or mixtures thereof. A lubricant can optionally be added, in an amount of less than about 1 weight percent of the pharmaceutical composition.

The composition may include a solubilizer to ensure good solubilization of the compound and to reduce precipitation of the compound of the present invention. A solubilizer may be used to increase solubility of the compound or other active ingredients, or may be used to maintain the composition as a homogeneous solution or dispersion. Examples of suitable solubilizers include but are not limited to, alcohols and polyols such as ethanol, isopopropanol, polyvinyl alcohol, gelatin, mannitol, sodium carboxymethyl cellulose (CMCNa), povidone, propylene glycol, polyethylene glycol, polyvinyl pyrolidone, glycerin, cyclodextrins or cyclodextrin derivatives, polyethylene glycol ethers of molecular weight averaging about 200 to about 6000, such as PEG, amides and other nitrogen-containing compounds such as 2-pyrrolidone, 2-piperidone, epsilon.-caprolactam, N-alkylpyrrolidone, N-hydroxyalkylpyrrolidone, N-alkylpiperidone, N-alkylcaprolactam, dimethylacetamide and polyvinylpyrrolidone, esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, water, or mixtures and/or combinations thereof.

Mixtures of solubilizers may also be used. Examples include, but not limited to, ethyl oleate, ethyl caprylate, triacetin, triethylcitrate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, transcutol, propylene glycol, glycofurol and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example, to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 75%, 100%, or up to about 200% by weight, based on the combined weight of the drug, and other excipients. If desired, very small amounts of solubilizer may also be used, such as 5%, 2%, 1%, 0.5% or even less. Typically, the solubilizer may be present in an amount of about 1% to about 100%, more typically about 5% to about 25% by weight.

The composition may include one or more pharmaceutically acceptable additives, which may include, but are not limited to, detackifiers, anti-foaming agents, buffering agents, antioxidants, polymers, preservatives, chelating agents, odorants, opacifiers, suspending agents, fillers, placstizers, and mixtures thereof.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the compound of Formula I or Formula II in the composition comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.0001% of the pharmaceutical composition by w/w, w/v or v/v.

In some embodiments, the concentration of the compound of Formula I or Formula II is in the range of about 0.0001% to about 50%, about 0.001% to about 40%, about 0.01% to about 20%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, or about 1% to about 10% of the pharmaceutical composition by w/w, w/v or v/v.

In some embodiments, the concentration of the compound of Formula I or Formula II is in the range of about 0.0001% to about 5%, about 0.001% to about 4%, about 0.01% to about 2%, about 0.02% to about 1%, or about 0.05% to about 0.5% of the pharmaceutical composition by w/w, w/v or v/v.

In some embodiments, the amount of the compound of Formula I or Formula II in the pharmaceutical composition is about 0.00001 mg, 0.0001 mg, 0.001 mg, 0.005 mg, 0.01 mg, 0.05 mg, 0.1 mg, 0.25 mg, 0.5 mg, 1 mg, 2 mg, 4 mg, 8 mg, 10 mg, 12 mg, 14 mg, 16 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 1.1 g, 1.2 g, 1.3 g, 1.4 g, 1.5 g, 1.6 g, 1.7 g, 1.8 g, 1.9 g, 2 g, 2.5 g, 3 g, 3.5 g, 4 g, 4.5 g, 5 g, 6 g, 7 g, 8 g, 9 g, or 10 g.

Described below are some non-limiting examples of pharmaceutical compositions.

Pharmaceutical Compositions for Oral Administration

The pharmaceutical composition comprising an effective amount of a compound of Formula I or Formula II can be formulated for oral administration. In some embodiments, the pharmaceutical composition comprising an effective amount of a compound of Formula I or Formula II for oral administration is a solid pharmaceutical composition. In some embodiments, the solid pharmaceutical composition may be presented as discrete (e.g., unit) oral dosage forms. Non-limiting examples of discrete oral dosage forms include tablets, capsules, caplets, gelatin capsules, sustained release formulations, lozenges, thin films, lollipops, and chewing gum.

Discrete oral dosage forms such as tablets may be coated by known techniques to delay or prolong absorption in the gastrointestinal tract, thus providing a sustained action of a longer period of time. In some embodiments, the compound of Formula I or Formula II is mixed with one or more inert solid diluents, such as calcium carbonate or calcium phosphate. In some embodiments, the compound of Formula I or Formula II is presented as soft gelatin capsules, wherein the compound is mixed with water or an oil medium, such as peanut oil, or olive oil, for example.

In some embodiments, the pharmaceutical composition comprising an effective amount of a compound of Formula I or Formula II for oral administration is a liquid pharmaceutical composition. Non-limiting examples of liquid compositions for oral administration include hydrophilic suspensions, emulsions, liquids, gels, syrups, slurries, solutions, elixirs, softgels, tinctures, and hydrogels. In some embodiments, solid or liquid compositions comprising an effective amount of a compound of Formula I or Formula II for oral administration comprise various sweetening or flavoring agents, or coloring agents. Examples of coloring agents include dyes suitable for food such as those known as F.D. & C. dyes and natural coloring agents such as grape skin extract, beet red powder, beta carotene, annato, carmine, turmeric, paprika, and so forth. Derivatives, analogues, and isomers of any of the above colored compound also may be used.

Such dosage forms may be prepared by methods well known to those skilled in the art, e.g., in a pharmacy. Such methods would comprise bringing the compound of Formula I or Formula II into association with the pharmaceutically acceptable carrier.

This invention further encompasses anhydrous pharmaceutical compositions and dosage forms comprising an effective amount of a compound of Formula I or Formula II, since water may facilitate the degradation of the compounds. In some embodiments, the anhydrous pharmaceutical compositions and dosage forms of the invention are prepared using anhydrous or low moisture containing ingredients. In some embodiments, the anhydrous pharmaceutical compositions and dosage forms of the invention are prepared under low humidity or low moisture conditions. The pharmaceutical compositions of the present invention which contain lactose may be made anhydrous if substantial contact with moisture and/or humidity during manufacturing, packaging, and/or storage is expected. An anhydrous pharmaceutical composition comprising an effective amount of a compound of Formula I or Formula II may be prepared and stored such that its anhydrous nature is maintained. For example, the anhydrous compositions may be packaged using materials known to prevent exposure to water such that they can be included in suitable formulary kits, examples of which include, but are not limited to, hermetically sealed foils, plastic or the like, unit dose containers, blister packs, and strip packs.

Pharmaceutical Compositions for Injection or Parenteral Administration

In some aspects, the pharmaceutical composition is formulated for parenteral administration. "Parenteral administration" generally refers to routes of administration other than the gastro-intestinal tract. Examples of parenteral administration include, but are not limited to, intravenous injection, subcutaneous injection, intramuscular injection, infusion, or implantation. Infusion may be intradermal, or subcutaneous, or through a transdermal implant. Exemplary pharmaceutical compositions for parenteral administration are disclosed in the following references which are hereby incorporated by reference: U.S. Patent Application Pub. No 2006/0287221, U.S. Pat. Nos. 5,244,925, 4,309,421, 4,158,707, and 5,164,405, all of which are hereby incorporated by reference.

Compositions formulated for parenteral administration may include aqueous solutions and/or buffers commonly used for injection and/or infusion. Commonly used aqueous buffers and/or solutions may include, but are not limited to sodium chloride solutions of about 0.9%, phosphate buffers, Lactated Ringer's solution, Acetated ringer's solution, phosphate buffered saline, citrate buffers, Tris buffers, histidine buffers, HEPES buffers, glycine buffers, N-glycylglycine buffers, and the like. Other pharmaceutically acceptable carriers for parenteral administration may include ethanol, glycerol, propylene glycol, cyclodextrin and cyclodextrin derivatives, vegetable oils, and the like.

In some embodiments, pharmaceutical compositions injection and/or infusion contain preservatives present in amounts that effectively prevent or reduce microbial contamination or degradation. Various agents, e.g., phenol, m-cresol, benzyl alcohol, parabens, chlorobutanol, methotrexate, sorbic acid, thimerosol, ethyl hydroxybenzoate, bismuth tribromophenate, methyl hydroxybenzoate, bacitracin, propyl hydroxybenzoate, erythromycin, 5-fluorouracil, doxorubicin, mitoxantrone, rifamycin, chlorocresol, benzalkonium chlorides, may be used to prevent or reduce contamination.

In some embodiments, sterile solutions are prepared by incorporating the compound of Formula I and/or II in the required amount in the appropriate solvent with various other ingredients as described herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain methods of preparation include but are not limited to vacuum-drying and freeze-drying techniques which yield a powder of the active ingredient plus any additional desired ingredient from a previously sterile-filtered solution thereof.

Other Pharmaceutical Compositions.

The pharmaceutical compositions employed in the present invention may be formulated for intraocular, topical, rectal, or intranasal administration. Formulations suitable for intraocular administration include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w. Formulations suitable for topical administration, e.g., in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising for example cocoa butter or a salicylate. Formulations suitable for intrapulmonary or nasal administration can have a particle size for example in the range of 0.1 to 500 microns (including particle sizes in a range between 0.1 and 500 microns in increments of microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of cancerous infections as described below. Preparations for such pharmaceutical compositions are described in, e.g., Anderson, Philip O.; Knoben, James E.; Troutman, William G., eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Exemplary Treatment Regiments and Routes of Administration

Administration of each compounds or pharmaceutical composition of the present invention can be performed by any method that enables delivery of the compound to the site of action. The composition may be administered orally, intraperitoneally, parenterally, intraocularly, topically, rectally, or intranasally. In some embodiments, the composition is administered orally. In some cases, the oral administration may comprise administration of any of the oral dosage forms as described herein. The effective amount of the compound of Formula I or Formula II administered will be dependent on the subject being treated, the severity of the disorder or condition, the rate of administration, the disposition of the compound and the discretion of the prescribing physician. A subject can be administered a daily dosage of lestaurtinib. The daily dosage can be from about 0.01 mg/kg to about 100 mg/kg of body weight per day. The daily dosage can be from about 0.01 mg/kg to 10 mg/kg of body weight per day. A daily dosage for an adult human can be about 1, 2, 3, 4, 5, 6, 7, 8, 9, 10, 12, 14, 16, 18, 20, 25, 30, 35, 40, 45, 50, 55, 60, 65, 70, 75, 80, 90, 100, 120, 140, 160, 180, 200, 300, 400, 500, 600, 700, 800, 900, or 1000 mg. Lestaurtinib can be administered in one or more unit dosage forms and can also be administered one to ten, one to eight, one to six, one to four, one to two times daily, or one time daily. A unit dosage form can comprise about 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 90, 100, 120, 140, 160, 180, 200, 300, 400, 500, 600, 700, 800, 900, or 1000 mg of lestaurtinib.

Dosages of lestaurtinib can also be in the form of liquids or suspensions in a concentration of between 15 to 25 mg/mL, 16 mg/mL or 25 mg/mL. The liquid or suspension dosage forms of lestaurtinib can include the equivalent of the doses (mg) described above. For example, dosages of lestaurtinib can include 1 to 5 mL of the 25 mg/mL solution, or 1, 1.2, 1.4, 1.6, 1.8, 2, 2.2, 2.4, 2.6, 2.8, 3, 3.2, 3.4, 3.6, 3.8, or 4 mL of the 25 mg/mL solution, wherein a 60 mg dose of lestaurtinib can be provided in 2.4 mL of solution, an 80 mg dose of lestaurtinib can be provided in 3.2 mL of solution and a 100 mg dose of lestaurtinib can be provided in 4 mL of solution. Additionally, a 20 mg dose of lestaurtinib can be provided with a 1.25 mL of a 16 mg/mL solution.

In some embodiments, administration may comprise infusion. In some cases, infusion may involve chronic, steady dosing. Devices for chronic, steady dosing, i.e., by a controlled pump, are known in the art, (examples may be described in U.S. Pat. Nos. 7,341,577, 7,351,239, 8,058,251, herein incorporated by reference).

Administration of the compound(s) of the invention may continue as long as necessary. In some embodiments, the compound(s) invention is administered for more than 1, 2, 3, 4, 5, 6, 7, 14, or 28 days. In some embodiments, the compound(s) invention is administered for more than 1 month, more than 2 months, more than 4 months, more than 6 months, more than 1 year, more than 2 years, or more than 5 years. In some embodiments, the compound(s) of the invention is administered for less than for less than 1 month, less than 2 months, less than 4 months, less than 6 months, less than 1 year, less than 2 years, or less than 5 years. In some embodiments, the compound(s) of the invention is administered for less than 28, 14, 7, 6, 5, 4, 3, 2, or 1 day. In some embodiments, an agent of the invention is administered chronically on an ongoing basis, e.g., for the treatment or prevention of a disease associated with elevated SPOP substrate level or its pathway activity.

It is known in the art that due to inter-subject variability in compound pharmacokinetics, individualization and/or adjustment of the dosing regimen may be necessary for optimal therapy. In some embodiments, a dosage is selected to achieve a blood serum level of about 0.05 to 20 µg/mL or from about 1 to 20 µg/mL of lestaurtinib in a subject.

Exemplary Combination Therapies

In some embodiments, the method comprises co-administration of an additional agent and a pharmaceutical composition comprising lestaurtinib. Additional agents may be: small molecules, nutraceuticals, vitamins, e.g., vitamin D, drugs, pro-drugs, biologics, peptides, peptide mimetics, antibodies, antibody fragments, cell or tissue transplants, vaccines, polynucleotides, DNA molecules, RNA molecules, (i.e., siRNA, miRNA), antibodies conjugated to drugs, toxins, fusion proteins. Agents may be delivered by vectors, including but not limited to plasmid vectors, viral vectors, non-viral vectors, liposomal formulations, nanoparticle formulations, toxins, therapeutic radioisotopes, etc.

In some embodiments, the additional agent is an antineoplastic agent. Non-limiting examples of anti-neoplastic agents include tubulin interacting agents, topoisomerase inhibitors and agents, acitretin, alstonine, amonafide, amphethinile, amsacrine, ankinomycin, anti-neoplaston, aphidicolin glycinate, asparaginase, baccharin, batracylin, benfluoron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphyrin ether, dihydrolenperone, dinaline, distamycin, docetaxel, ellipr-abin, elliptinium acetate, epothilones, ergotamine, etoposide, etretinate, fenretinide, gallium nitrate, genkwadaphnin, hexadecylphosphocholine, HDAC inhibitors, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, octreotide, oquizanocine, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, and withanolides.

In some embodiments, the additional agent is an anti-cancer agent. Non-limiting examples of anti-cancer agents include acemannan, aclarubicin, aldesleukin, alemtuzumab, alitretinoin, altretamine, amifostine, amsacrine, anagrelide, anastrozole, ancestim, bexarotene, broxuridine, capecitabine, celmoleukin, cetrorelix, cladribine, clotrimazole, daclizumab, dexrazoxane, dilazep, docosanol, doxifluridine, bromocriptine, carmustine, cytarabine, diclofenac, edelfosine, edrecolomab, eflornithine, emitefur, exemestane, exisulind, fadrozole, erythropoietin, filgrastim, finasteride, fludarabine phosphate, formestane, fotemustine, gallium nitrate, gemcitabine, glycopine, heptaplatin, ibandronic acid, imiquimod, iobenguane, irinotecan, irsogladine, lanreotide, leflunomide, lenograstim, lentinan sulfate, letrozole, liarozole, lobaplatin, lonidamine, masoprocol, melarsoprol, metoclopramide, mifepristone, miltefosine, mirimostim, mitoguazone, mitolactol, molgramostim, nafarelin, nartograstim, nedaplatin, nilutamide, noscapine, oprelvekin, osaterone, oxaliplatin, pamidronic acid, pegaspargase, pentosan polysulfate sodium, pentostatin, picibanil, pirarubicin, porfimer sodium, raloxifene, raltitrexed, rasburicase, rituximab, romurtide, sargramostim, sizofuran, sobuzoxane, sonermin, suramin, tasonermin, tazarotene, tegafur, temoporfin, temozolomide, teniposide, tetrachlorodecaoxide, thalidomide, thrombopoietin, thymalfasin, thyrotropin alfa, topotecan, toremifene, trastuzumab, treosulfan, tretinoin, trilostane, trimetrexate, ubenimex, valrubicin, verteporfin, and vinorelbine.

In some embodiments, the additional agent is an anti-androgen. Exemplary anti-androgens include bicalutamide, flutamide, spironolactone, cyproterone acetate, finasteride, dutasteride, enzalutamide, ketoconazole, abiraterone, galeterone, and nilutamide.

In some embodiments, the additional agent is an agent that promotes autophagy. The autophagy-promoting agent can be an mTOR or mTOR pathway inhibitor. Exemplary mTOR and/or mTOR pathway inhibitors include, but are not limited to rapamycin, temsirolimus, umirolimus, zotarolimus, TOR kinase inhibitors such as, e.g., OSI-027, INK-128, AZD-8055, AZD-2014, Palomid 529, Pp-242, BEZ235, AZD-8055, BGT226, XL765, GDC-0980, GSK2126458, PF-04691502, PF-05212384 analogues or derivatives thereof.

In some embodiments, the additional agent is a PI3K inhibitor. Exemplary PI3K inhibitors include, but are not limited to SF1126, SF1101, BEZ235, BKM120, BYL719, BGT-226, XL-147, GDC-0941, ZSTK-474, PX-866, GDC-0980, PKI-587, PF-04691502, BWT33597, PI-103, CAL-101, GNE-477 or any derivatives thereof.

Dosages of the additional agent and of lestaurtinib can vary depending on the type of additional therapeutic agent employed, on the disease or condition being treated and so forth. Sub-therapeutic amounts of one or both of the additional agent and lestaurtinib can be used. Therapeutically effective amounts of one or both of the additional agent and lestaurtinib can be used. Lestaurtinib and the additional agent may be administered either simultaneously or sequentially. If administered sequentially, the attending physician or caretaker can decide on the appropriate sequence of administering the compound and the additional therapeutic agent.

Kits

The invention also provides kits. Kits of the invention can comprise at least one or more unit dosages of a pharmaceutical composition described herein, in suitable packaging, and instructions for use in carrying out one or more methods of the invention. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Examples of suitable packaging include, but are not limited to, hermetically sealed foils, plastic or the like, unit dose containers, blister packs, and strip packs.

EXAMPLES

Example 1

Materials and Methods

Materials and cell lines: Prostate, breast and gastric cancer cell lines and their sources are shown in the table below. The growth condition of each tumor cell line is shown in the subsequent table per recommendation from ATCC. Staurosporine (from Sigma, Cat. No. S4400-1mg, Lot No. 017k4059) and Lestaurtinib (from Sigma, Cat. No. C7869-1mg, Lot No. 072M4750V) were dissolved in DMSO (Sigma).

| Cell Line | Vendor | Cat# | Description |
|---|---|---|---|
| PC-3 | ATCC | CRL-1435 | prostate, adenocarcinoma |
| 22RV1 | SIBS | TCHu 100 | prostate, carcinoma |
| DU145 | ATCC | HTB-81 | prostate, carcinoma |
| LNCaP Clone FGC | ATCC | CRL-1740 | prostate, carcinoma |
| AGS | ATCC | CRL-1739 | stomach, gastric adenocarcnoma |
| MKN-45 | JCRB | JCRB0254 | stomach, gastric adenocarcinoma |
| Hs746T | ATCC | HTB-135 | stomach, gastric carcinoma |
| NCI-N87 | ATCC | CRL-5822 | stomach, gastric carcinoma |
| MCF7 | ATCC | HTB-22 | breast, adenocarcinoma (pleural effusion) |
| BT-474 | ATCC | HTB-20 | breast, ductal carcinoma |
| ZR-75-1 | ATCC | CRL-1500 | breast, ductal carcinoma |

| Cell Line | Complete medium | Seeding Density (96-well, per well) | Incubation Time (hr) |
|---|---|---|---|
| PC-3 | F-12K + 10% FBS | 3000 | 72 |
| 22RV1 | RPMI1640 + 10% FBS | 6000 | 72 |
| DU145 | DMEM + 10% FBS | 5000 | 72 |
| LNCaP Clone FGC | RPMI1640 + 10% FBS | 5000 | 72 |
| AGS | F-12K + 10% FBS | 2500 | 48 |
| MKN-45 | RPMI1640 + 10% FBS | 2500 | 72 |
| Hs746T | DMEM + 10% FBS | 2000 | 72 |
| NCI-N87 | RPMI1640 + 10% FBS | 4000 | 72 |
| MCF7 | Eagle's Minimum Essential Medium + 0.01 mg/ml bovine insulin + 10% FBS | 4000 | 72 |
| BT-474 | Hybricare + 10% FBS | 12000 | 72 |
| ZR-75-1 | RPMI1640 + 10% FBS | 3000 | 72 |

Cell proliferation assay: MTT assay was used to determine growth suppression of prostate cancer cells by lestaurtinib. Cells were plated in 96-well plates with 60% confluence, and incubated with 0.1% DMSO (control), 10, 30, 100, 300, 1000, 3000 nM lestaurtinib for 48 hours before MTT assay. Each concentration of lestaurtinib was repeated at least 3 times to minimize variation. The MTT reagent (CellTiter 96® Aqueous One Solution Reagent by Promega™) was mixed with the DMEM media, and 100 µl of the mixture was pipetted into each well. The color of the medium changed from yellow/brown to dark brown, which indicated that MTS tetrazolium was converted to formazan. Formazan was then quantified by a plate reader SpectraMax M5. A blank well with MTT mixture only was also obtained for background subtraction.

Protein analysis in cell lysates: Protein concentrations were determined by the colorimetric method using BioRad protein analysis reagents. In brief, 2 µL of cell lysates were mixed with 1 mL 1:5 diluted reagent and OD595 was determined by the SmartSpec 3000™ spectrophotometer (Bio Rad). Equal amounts of proteins were analyzed with SDS-PAGE (sodium dodecyl sulfate polyacrylamide gel electrophoresis) using 4-20% Criterion™ TGX™ Precast Gels. Prestained protein standards were added for co-migration with samples to estimate molecular weights. Once electrophoresis was completed, proteins were transferred from gel to nitrocellulose membrane for Western blotting. Ponceau S was used to stain proteins. Membrane was first incubated with 5% milk in TBST (Tris-buffered saline-Tween 20) to block non-specific binding for 1 hour followed by incubation with primary antibody (1:1000 dilution) overnight. After membrane was washed 3 times with TBST for 30 minutes, horseradish peroxidase-conjugated secondary anti-rabbit antibody was added for incubation for another 60 min. Chemiluminescence and X-ray films were used to detect the bands. Rabbit polyclonal antibody (5E11) against SRC-3 was purchased from Cell Signaling Technology (Boston, Mass.). Rabbit polyclonal antibody against PRK1 (07-557) was from Upstate/Millipore (Billerica, Mass.).

Subcellular Fractionation: Subcellular fractionation was performed to separate nuclei and cytoplasm from cells. PC3, DU145 and LNCaP cells were incubated with 0.1% DMSO (control) or 1 µM lestaurtinib for 6 hours before harvest for subcellular fractionation. A hypotonic lysis buffer containing 1 mM EDTA (ethylenediamine tetra-acetic acid), 0.1×PBS (Phosphate Buffered Saline), and a battery of proteasome inhibitor was added to the cells for 5 min. The cells were scraped and broken by shearing 25 times with 27G needles in tuberculin syringes. Nuclei were pelleted first with centrifugation at 3,000 rpm at 4° C. for 10 minutes, and then supernatants were centrifuged at 15,000 rpm at 4° C. for 10 minutes and the supernatants were used as cytoplasm. The whole cell lysates, nuclear fractions and cytoplasmic fractions were used for protein analysis and Western blotting. Antibodies against tubulin, actin and histone were used for loading and localization controls.

Example 2

Searching for SPOP Substrates

PubMed search of SPOP-dependent protein degradation revealed that SRC-3, Daxx, and Gli are the known substrates of SPOP Biol Chem. 2006; 281:12664-72, Oncogene 2011; 30:4350-64, Dev Cell. 2006; 10: 719-29). We searched NCBI database with an attempt to identify other SPOP substrates that are involved in androgen receptor signaling. Structural database in the NCBI revealed that three peptide sequences can interact with SPOP. These include:

(SEQ ID NO: 7)
KAASADSTTEGTPAD (http://www.ncbi.nlm.nih.gov/Structure/mmdb/mmdb-srv.cgi?uid=77512)

(SEQ ID NO: 8)
NTLFPDVSSSTH (http://www.ncbi.nlm.nih.gov/Structure/mmdb/mmdb-srv.cgi?uid=77549)

(SEQ ID NO: 9)
DEVTSTTSSS (http://www.ncbi.nlm.nih.gov/Structure/mmdb/mmdbsrv.cgi?uid=77550)

All three peptide sequences are consistent with the consensus sequence of multiple Ser/Thr followed by an acidic residue previously reported (Proc Natl Acad Sci USA. 2009; 106: 21191-6). We performed a BLAST search using the consensus sequences in order to identify other proteins with the consensus sequence, which might be potential SPOP substrates that were not recognized in the past. A BLAST search with DSTSS resulted in a number of matches. Four exemplary matches are listed below.

```
gi|339276078|ref|NP_001229847.1|AN1-type zinc
finger protein 6 isoform c [Homo sapiens]
                                 (SEQ ID NO: 10)
MAQETNHSQVPMLCSTGCGFYGNPRTNGMCSVCYKEHLQRQNSSNGRISP

PATSVSSLSESLPVQCTDGSVPEAQSALDSTSSSMQPSPVSNQSLLSESV

ASSQLDSTSVDKAVPETEDVQGFECRCGNVYCGVHRYSDVHNCSYNYKAD

AAEKIRKENPVVVGEKIQKI gi|62739157|ref|NP_001014988.1|linker for activa-
tion of T-cells family member 1 isoform c [Homo
sapiens]
                                 (SEQ ID NO: 11)
MEEAILVPCVLGLLLLPILAMLMALCVHCHRLPGSYDSTSSDSLYPRGIQ

FKRPHTVAPWPPAYPPVTSYPPLSQPDLLPIPSPQPLGGSHRTPSSRRDS

DGANSVASYENEEPACEDADEDEDDYHNPGYLVVLPDSTPATSTAAPSAP

ALSTPGIRDSAFSMESIDDYVNVPESGESAEASLDGSREYVNVSQELHPG

AAKTEPAALSSQEAEEVEEEGAPDYENLQELN gi|121114298|ref|NP_003579.3| cullin-4B isoform 1
[Homo sapiens]
                                 (SEQ ID NO: 12)
MMSQSSGSGDGNDDEATTSKDGGFSSPSPSAAAAAQEVRSATDGNTSTTP

PTSAKKRKLNSSSSSSSNSSNEREDFDSTSSSSSTPPLQPRDSASPSTSS

FCLGVSVAASSHVPIQKKLRFEDTLEFVGFDAKMAEESSSSSSSSSPTAA

TSQQQQLKNKSILISSVASVHHANGLAKSSTTVSSFANSKPGSAKKLVIK

NFKDKPKLPENYTDETWQKLKEAVEAIQNSTSIKYNLEELYQAVENLCSY

KISANLYKQLRQICEDHIKAQIHQFREDSL gi|41872646|ref|NP_055595.2| cullin-7 isoform 2
[Homo sapiens]
                                 (SEQ ID NO: 13)
WEKVEVSSNPHRASKLTDHNPKTYWESNGSAGSHYITLHMRRGILIRQLT

LLVASEDSSYMPARVVVCGGDSTSSLHTELNSVNVMPSASRVILLENLTR

FWPIIQIRIKRCQQGGIDTRIRGLEILGPKPTFWPVFREQLCRHTRLFYM

VRAQAWSQDMAEDRRSLLHLSSRLNGALRQEQNFADRFLPDDEAAQALGK

TCWEALVSPV
```

Another BLAST search by a sequence DSSTT identified DEK (NCBI Reference Sequence: NP_003463.1)

```
>gi|4503249|ref|NP_003463.1| protein DEK isoform 1
[Homo sapiens]
                                 (SEQ ID NO: 14)
MSASAPAAEGEGTPTQPASEKEPEMPGPREESEEEEDEDDEEEEEEEKEK

SLIVEGKREKKKVERLTMQVSSLQREPFTIAQGKGQKLCEIERIHFFLSK

KKTDELRNLHKLLYNRPGTVSSLKKNVGQFSGFPFEKGSVQYKKKEEMLK

KFRNAMLKSICEVLDLERSGVNSELVKRILNFLMHPKPSGKPLPKSKKTC

SKGSKKERNSSGMARKAKRTKCPEILSDESSSDEDEKKNKEESSDDEDKE

SEEEPPKKTAKREKPKQKATSKSKKSVKSANVKKADSSTTKKNQNSSKKE

SESEDSSDDEPLIKKLKKPPTDEELKETIKKLLASANLEEVTMKQICKKV

YENYPTYDLTERKDFIKTTVKELIS
```

Example 3

Sensitivity of Prostate, Breast and Gastric Cancer Cells Against Lestaurtinib To examine the feasibility of using lestaurtinib to treat prostate, breast, gastric and other cancers, three prostate cancer cell lines with varying degrees of androgen sensitivity, PC3 (androgen insensitive), DU145 (androgen insensitive), and LNCaP (androgen sensitive), were investigated in their sensitivity against lestaurtinib (FIG. 2A-C). Three breast cancer cell lines, MCF7, BT-474, and ZR-75-1 (FIG. 3A-C), and four gastric cancer cell lines, AGS, MKN-45, Hs746T and NCI-N87 (FIG. 4A-D), were also tested to determine their $IC_{50}$ against lestaurtinib and compared with staurosporine, a lestaurtinib homologue with much broader kinase inhibitory activity. All tumor cells were treated with DMSO (control) or 10, 30, 100, 300, 1000, or 3000 nM lestaurtinib or staurosporine for 48 hours. MTT assays were then performed to determine the impact of drug treatment on tumor cell viability. $IC_{50}$ was determined as the concentration of lestaurtinib that achieved half maximal decrease in cell viability. As shown in FIG. 2-4, lestaurtinib was effective in reducing viability of prostate and gastric cancer cells, whereas breast cancer cells were more resistant against lestaurtinib with higher $IC_{50}$. The $IC_{50}$ for each tumor cell line is summarized in FIG. 5.

Example 4

Levels of SRC-3 and PRK1 Protein Expression in Prostate Cancer Cells

Using Western blotting, the levels of SRC-3 protein expression were examined in the three prostate cancer cell lines before and after lestaurtinib treatment. LNCaP, DU145 and PC3 cells were treated with 1 µM lestaurtinib for 6 hours and harvested for subcellular fractionation. Whole cell lysates, nuclear fractions, and cytosolic fractions were analyzed with Western blotting using various antibodies. Actin, tubulin and Histone-H3 were used as loading and localization controls.

Figure 6:
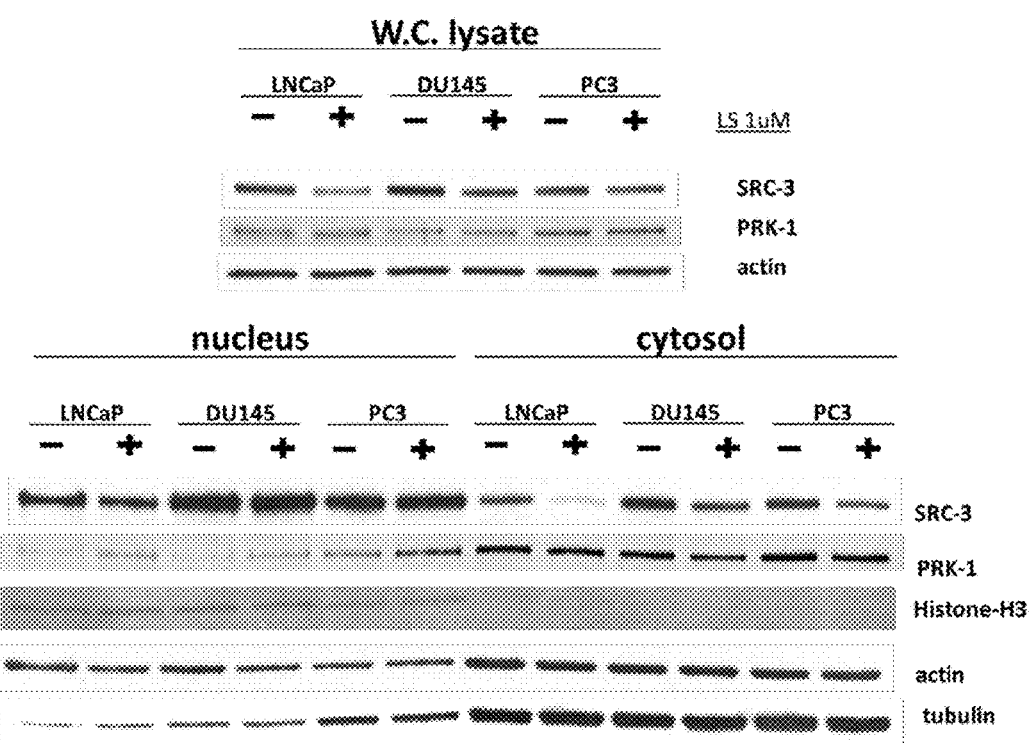
FIG. 6 depicts the impact of lestaurtinib on SRC-3 and PRK1 protein expression levels in prostate cancer cell lines.

Untreated LNCaP, PC3 and DU145 cells exhibited similar levels of SRC-3 protein expression (FIG. 6, top panel). However, lestaurtinib-treated LNCaP cells exhibited a profound decrease of SRC-3, whereas SRC-3 protein levels in lestaurtinib-treated PC3 and DU145 cells were not significantly altered (FIG. 6, top panel). By contrast, the PRK1 protein expression levels were not significantly altered by lestaurtinib treatment in any of the tested cell lines.

Example 5

Changes of SRC-3 and PRK1 Proteins in Nucleus and Cytoplasm

The effect of lestaurtinib treatment on intracellular localization of SRC-3 and PRK was investigated in the three prostate cancer cell lines using subcellular fractionation studies. LNCaP, PC3, and DU145 cell lines were treated with 1000 nM lestaurtinib or control vehicle for 6 hours. Nuclear and cytosolic fractions were obtained and analyzed by western blot. Antibodies used include SRC-3, PRK, tubulin, histone-H3, and actin. Western blot analysis revealed that lestaurtinib treatment reduced SRC-3 protein in the cytoplasm of all three cell lines. The reduction in cytoplasmic SRC-3 was much more dramatic in lestaurtinib-treated LNCaP cells as compared to lestaurtinib-treated PC3 or DU145 cells (FIG. 6, bottom panel). Lestaurtinib treatment did not caused a reduction in nuclear SRC-3 protein levels in LNCaP, DU145 or PC3 cells (FIG. 6, bottom panel). By contrast, nuclear PRK-1 protein levels were increased by lestaurtinib treatment in all three cell lines, while cytoplasmic PRK-1 levels were unaltered by lestaurtinib treatment (FIG. 6, bottom panel).

Figure 7:
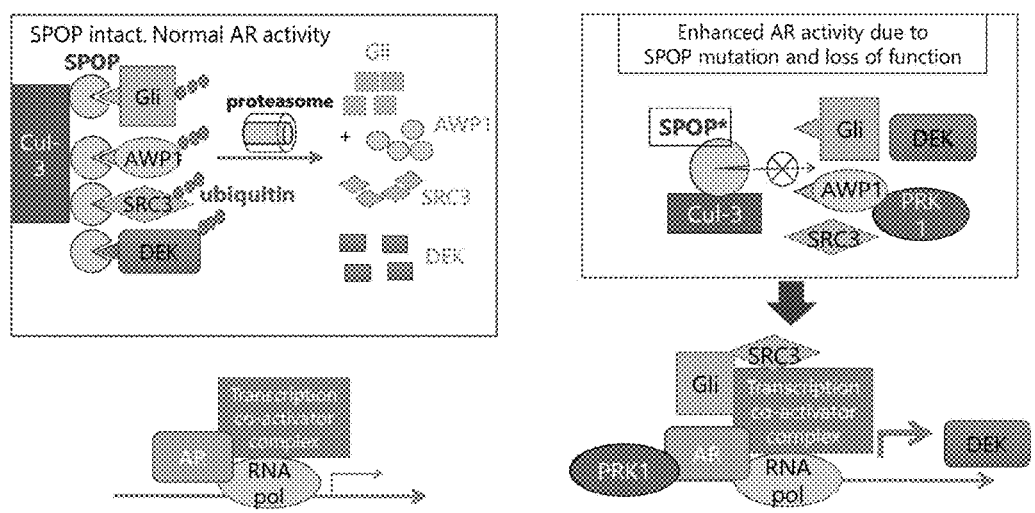
FIG. 7 depicts a working model of AR transcriptional activity regulation in cells with wild-type versus mutant SPOP.

Based on the above data, a model was proposed (FIG. 7). In cells with normal levels of SPOP activity, SPOP substrates such as Gli, SRC-3 and AWP1 can be degraded through SPOP-dependent protein degradation, which regulates AR activity (left panel, FIG. 7). However, in prostate cancer cells with reduced SPOP activity (such as, e.g., prostate cancer cells with mutated SPOP), degradation of SPOP substrates such as SRC-3, Gli, AWP1, by SPOP is impaired, resulting in accumulation of the SPOP substrates and enhanced AR and/or prosurvival pathway activity. It was found that lestaurtinib mediated cell death of androgen-dependent prostate cancer cells is correlated with a significant reduction levels of SRC3, an SPOP substrate that acts as an Androgen Receptor co-activator. This data indicates that lestaurtinib can be used to effectively treat diseases in subjects having aberrantly high levels of SPOP substrate or substrate pathway activity, such as in subjects having of SPOP mutations and/or high SRC3 levels. This mechanism provides a rationale-based approach to interrupt activation of androgen receptor by blocking the process.

Example 6

Changes of SRC3 and DEK Protein Levels in Prostate, Breast and Gastric Cancer Cells Based on their sensitivity against lestaurtinib, LNCaP and PC3 prostate cancer cells, MCF7 and ZR75-1 breast cancer cells, and MKN-45 and NCI-N87 gastric cancer cells were chosen to test the levels of expression before and 24 hours after treated with two different doses of lestaurtinib. Doses that achieved approximately 40% and 70% growth inhibition were chosen for treatment and examined for the Western blotting. For prostate cancer shown in FIG. 8, SRC3 protein levels decreased in the higher dose treated cells, but no obvious changes were seen in DEK protein levels. For breast cancer shown in FIG. 9, MCF7 had the highest levels of SRC3 in baseline and exhibited the most profound dose-dependent decrease after lestaurtinib treatment. ZR75-1 had much lower levels of SRC3 but no obvious change after treatment. However both MCF7 and ZR75-1 cells had decreased DEK protein levels after treatment. In gastric cancer shown in FIG. 10, SRC3 expression levels showed a decrease in MKN-45 cells after treatment with higher dose of lestaurtinib, but not in NCI-N87. DEK levels did not change after lestaurtinib treatment as shown in FIG. 10.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a symptom of a prostate tumor in a subject, comprising administering to the subject a pharmaceutical composition comprising a therapeutically effective amount of lestaurtinib or pharmaceutically acceptable salt thereof, thereby downregulating a speckle-type POZ protein ("SPOP") substrate in the subject, wherein the subject exhibits an aberrantly high level of the SPOP substrate as compared to a control subject, and wherein the aberrantly high level of the SPOP substrate is evidenced by a presence of an SPOP mutation in the subject, thereby treating the symptom of the prostate tumor in the subject.

2. The method of claim 1, wherein the SPOP substrate is selected from the group consisting of SRC1, SRC2, SRC3, Daxx, Gli, AWP-1, cullin-4B, and cullin-7, and DEK.

3. The method of claim 1, wherein the downregulating comprises decreasing a level and/or activity of the SPOP substrate.

4. The method of claim 3, wherein the downregulating comprises decreasing the level of the SPOP substrate.

5. The method of claim 3, wherein the downregulating is evidenced by (i) a reduction in a level of the SPOP substrate in a cell derived from the subject or (ii) a reduction in a level of the SPOP substrate in a cytoplasmic fraction of the cell.

6. The method of claim 3, wherein the level comprises an expression level.

7. The method of claim 6, wherein the expression level is a protein expression level.

8. The method of claim 6, wherein the expression level is evidenced by a level of a transcript of the SPOP substrate.

9. The method of claim 1, wherein the administering comprises:

(a) administering to the subject a first dose of the pharmaceutical composition comprising Hall the therapeutically effective amount of lestaurtinib or pharmaceutically acceptable salt thereof; and wherein the method further comprises:

(b) determining the SPOP substrate level or activity of the SPOP substrate in a biological sample derived from the subject; and (c) administering an additional dose of the pharmaceutical composition if the substrate level or its activity is reduced as compared to a control subject that is not administered a pharmaceutical composition comprising a therapeutically effective amount of lestaurtinib or pharmaceutically acceptable salt thereof.

10. The method of claim 1, wherein the SPOP mutation results in an altered amino acid sequence between positions 31-161 of an SPOP amino acid sequence.

11. The method of claim 10, wherein the altered amino acid sequence comprises an amino acid substitution.

12. The method of claim 1, wherein the SPOP mutation causes a substitution at Y87, F102, S119, F125, K129, W131, F133, and/or K134 of the SPOP amino acid sequence.

13. The method of claim 1, wherein the subject is a human.

14. The method of claim 1, wherein the prostate tumor is androgen sensitive.

15. The method of claim 1, wherein the prostate tumor is androgen insensitive.

16. The method of claim 3, wherein the downregulating comprises decreasing the activity of the SPOP substrate.

* * * * *

UNITED STATES PATENT AND TRADEMARK OFFICE
CERTIFICATE OF CORRECTION

Page 1 of 1

PATENT NO. : 10,449,202 B2
APPLICATION NO. : 15/653480
DATED : October 22, 2019
INVENTOR(S) : Allen J. Lee et al.

It is certified that error appears in the above-identified patent and that said Letters Patent is hereby corrected as shown below:

On the Title Page

Column 1, Item (72), Inventors:
Replace "David M. Lu, Richmond, NJ (US)" with --David M. Lu, Richmond, VA (US)--

In the Claims

Column 52, Line 11, Claim 9, Paragraph (a):
Replace "composition comprising Hall the" with --composition comprising the--

Column 52, Line 15, Claim 9, Paragraph (b):
Replace "determining the SPOP substrate level" with --determining a substrate level--

Column 52, Line 31, Claim 12:
Replace "and/or K134 of the SPOP amino acid" with --and/or K134 of an SPOP amino acid--

Signed and Sealed this
Thirty-first Day of December, 2019

Andrei Iancu
*Director of the United States Patent and Trademark Office*

SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

```
Asp Ser Thr Thr
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Val Ser Ser Thr
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Val Thr Ser Thr Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ser Thr Ser Ser
1               5

<210> SEQ ID NO 5
<211> LENGTH: 5
<212> TYPE: PRT
<213> ORGANISM: Homo sapiens

<400> SEQUENCE: 5

Asp Ser Ser Thr Thr
1               5

<210> SEQ ID NO 6
<211> LENGTH: 5
<212> TYPE: PRT
<213> ORGANISM: Homo sapiens

<400> SEQUENCE: 6

Asp Glu Ser Ser Ser
1               5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ala Ala Ser Ala Asp Ser Thr Thr Glu Gly Thr Pro Ala Asp
```

```
<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Thr Leu Phe Pro Asp Val Ser Ser Ser Thr His
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Glu Val Thr Ser Thr Thr Ser Ser Ser
1               5                   10

<210> SEQ ID NO 10
<211> LENGTH: 170
<212> TYPE: PRT
<213> ORGANISM: Homo sapiens

<400> SEQUENCE: 10

Met Ala Gln Glu Thr Asn His Ser Gln Val Pro Met Leu Cys Ser Thr
1               5                   10                  15

Gly Cys Gly Phe Tyr Gly Asn Pro Arg Thr Asn Gly Met Cys Ser Val
                20                  25                  30

Cys Tyr Lys Glu His Leu Gln Arg Gln Asn Ser Ser Asn Gly Arg Ile
            35                  40                  45

Ser Pro Pro Ala Thr Ser Val Ser Ser Leu Ser Glu Ser Leu Pro Val
        50                  55                  60

Gln Cys Thr Asp Gly Ser Val Pro Glu Ala Gln Ser Ala Leu Asp Ser
65                  70                  75                  80

Thr Ser Ser Ser Met Gln Pro Ser Pro Val Ser Asn Gln Ser Leu Leu
                85                  90                  95

Ser Glu Ser Val Ala Ser Ser Gln Leu Asp Ser Thr Ser Val Asp Lys
                100                 105                 110

Ala Val Pro Glu Thr Glu Asp Val Gln Gly Phe Glu Cys Arg Cys Gly
            115                 120                 125

Asn Val Tyr Cys Gly Val His Arg Tyr Ser Asp Val His Asn Cys Ser
        130                 135                 140

Tyr Asn Tyr Lys Ala Asp Ala Ala Glu Lys Ile Arg Lys Glu Asn Pro
145                 150                 155                 160

Val Val Val Gly Glu Lys Ile Gln Lys Ile
                165                 170

<210> SEQ ID NO 11
<211> LENGTH: 232
<212> TYPE: PRT
<213> ORGANISM: Homo sapiens

<400> SEQUENCE: 11
```

```
Met Glu Glu Ala Ile Leu Val Pro Cys Val Leu Gly Leu Leu Leu Leu
1               5                   10                  15

Pro Ile Leu Ala Met Leu Met Ala Leu Cys Val His Cys His Arg Leu
            20                  25                  30

Pro Gly Ser Tyr Asp Ser Thr Ser Ser Asp Ser Leu Tyr Pro Arg Gly
            35                  40                  45

Ile Gln Phe Lys Arg Pro His Thr Val Ala Pro Trp Pro Pro Ala Tyr
50                  55                  60

Pro Pro Val Thr Ser Tyr Pro Pro Leu Ser Gln Pro Asp Leu Leu Pro
65                  70                  75                  80

Ile Pro Ser Pro Gln Pro Leu Gly Gly Ser His Arg Thr Pro Ser Ser
            85                  90                  95

Arg Arg Asp Ser Asp Gly Ala Asn Ser Val Ala Ser Tyr Glu Asn Glu
            100                 105                 110

Glu Pro Ala Cys Glu Asp Ala Asp Glu Asp Asp Tyr His Asn
            115                 120                 125

Pro Gly Tyr Leu Val Val Leu Pro Asp Ser Thr Pro Ala Thr Ser Thr
            130                 135                 140

Ala Ala Pro Ser Ala Pro Ala Leu Ser Thr Pro Gly Ile Arg Asp Ser
145                 150                 155                 160

Ala Phe Ser Met Glu Ser Ile Asp Asp Tyr Val Asn Val Pro Glu Ser
                165                 170                 175

Gly Glu Ser Ala Glu Ala Ser Leu Asp Gly Ser Arg Glu Tyr Val Asn
            180                 185                 190

Val Ser Gln Glu Leu His Pro Gly Ala Ala Lys Thr Glu Pro Ala Ala
            195                 200                 205

Leu Ser Ser Gln Glu Ala Glu Glu Val Glu Glu Glu Gly Ala Pro Asp
210                 215                 220

Tyr Glu Asn Leu Gln Glu Leu Asn
225                 230

<210> SEQ ID NO 12
<211> LENGTH: 280
<212> TYPE: PRT
<213> ORGANISM: Homo sapiens

<400> SEQUENCE: 12

Met Met Ser Gln Ser Ser Gly Ser Gly Asp Gly Asn Asp Asp Glu Ala
1               5                   10                  15

Thr Thr Ser Lys Asp Gly Gly Phe Ser Ser Pro Ser Pro Ser Ala Ala
            20                  25                  30

Ala Ala Ala Gln Glu Val Arg Ser Ala Thr Asp Gly Asn Thr Ser Thr
            35                  40                  45

Thr Pro Pro Thr Ser Ala Lys Lys Arg Lys Leu Asn Ser Ser Ser Ser
50                  55                  60

Ser Ser Ser Asn Ser Ser Asn Glu Arg Glu Asp Phe Asp Ser Thr Ser
65                  70                  75                  80

Ser Ser Ser Ser Thr Pro Pro Leu Gln Pro Arg Asp Ser Ala Ser Pro
            85                  90                  95

Ser Thr Ser Ser Phe Cys Leu Gly Val Ser Val Ala Ala Ser Ser His
            100                 105                 110

Val Pro Ile Gln Lys Lys Leu Arg Phe Glu Asp Thr Leu Glu Phe Val
            115                 120                 125

Gly Phe Asp Ala Lys Met Ala Glu Glu Ser Ser Ser Ser Ser Ser Ser
            130                 135                 140
```

-continued

Ser Ser Pro Thr Ala Ala Thr Ser Gln Gln Gln Leu Lys Asn Lys
145                 150                 155                 160

Ser Ile Leu Ile Ser Ser Val Ala Ser Val His His Ala Asn Gly Leu
            165                 170                 175

Ala Lys Ser Ser Thr Thr Val Ser Ser Phe Ala Asn Ser Lys Pro Gly
        180                 185                 190

Ser Ala Lys Lys Leu Val Ile Lys Asn Phe Lys Asp Lys Pro Lys Leu
            195                 200                 205

Pro Glu Asn Tyr Thr Asp Glu Thr Trp Gln Lys Leu Lys Glu Ala Val
        210                 215                 220

Glu Ala Ile Gln Asn Ser Thr Ser Ile Lys Tyr Asn Leu Glu Glu Leu
225                 230                 235                 240

Tyr Gln Ala Val Glu Asn Leu Cys Ser Tyr Lys Ile Ser Ala Asn Leu
                245                 250                 255

Tyr Lys Gln Leu Arg Gln Ile Cys Glu Asp His Ile Lys Ala Gln Ile
            260                 265                 270

His Gln Phe Arg Glu Asp Ser Leu
            275                 280

<210> SEQ ID NO 13
<211> LENGTH: 210
<212> TYPE: PRT
<213> ORGANISM: Homo sapiens

<400> SEQUENCE: 13

Trp Glu Lys Val Glu Val Ser Ser Asn Pro His Arg Ala Ser Lys Leu
1               5                   10                  15

Thr Asp His Asn Pro Lys Thr Tyr Trp Glu Ser Asn Gly Ser Ala Gly
            20                  25                  30

Ser His Tyr Ile Thr Leu His Met Arg Arg Gly Ile Leu Ile Arg Gln
        35                  40                  45

Leu Thr Leu Leu Val Ala Ser Glu Asp Ser Ser Tyr Met Pro Ala Arg
    50                  55                  60

Val Val Val Cys Gly Gly Asp Ser Thr Ser Ser Leu His Thr Glu Leu
65                  70                  75                  80

Asn Ser Val Asn Val Met Pro Ser Ala Ser Arg Val Ile Leu Leu Glu
                85                  90                  95

Asn Leu Thr Arg Phe Trp Pro Ile Ile Gln Ile Arg Ile Lys Arg Cys
            100                 105                 110

Gln Gln Gly Gly Ile Asp Thr Arg Ile Arg Gly Leu Glu Ile Leu Gly
        115                 120                 125

Pro Lys Pro Thr Phe Trp Pro Val Phe Arg Glu Gln Leu Cys Arg His
    130                 135                 140

Thr Arg Leu Phe Tyr Met Val Arg Ala Gln Ala Trp Ser Gln Asp Met
145                 150                 155                 160

Ala Glu Asp Arg Arg Ser Leu Leu His Leu Ser Ser Arg Leu Asn Gly
                165                 170                 175

Ala Leu Arg Gln Glu Gln Asn Phe Ala Asp Arg Phe Leu Pro Asp Asp
            180                 185                 190

Glu Ala Ala Gln Ala Leu Gly Lys Thr Cys Trp Glu Ala Leu Val Ser
        195                 200                 205

Pro Val
    210

<210> SEQ ID NO 14
<211> LENGTH: 375
<212> TYPE: PRT
<213> ORGANISM: Homo sapiens

<400> SEQUENCE: 14

Met Ser Ala Ser Ala Pro Ala Ala Glu Gly Glu Gly Thr Pro Thr Gln
1               5                   10                  15

Pro Ala Ser Glu Lys Glu Pro Glu Met Pro Gly Pro Arg Glu Glu Ser
            20                  25                  30

Glu Glu Glu Glu Asp Glu Asp Asp Glu Glu Glu Glu Glu Glu Glu Lys
        35                  40                  45

Glu Lys Ser Leu Ile Val Glu Gly Lys Arg Glu Lys Lys Lys Val Glu
    50                  55                  60

Arg Leu Thr Met Gln Val Ser Ser Leu Gln Arg Glu Pro Phe Thr Ile
65                  70                  75                  80

Ala Gln Gly Lys Gly Gln Lys Leu Cys Glu Ile Glu Arg Ile His Phe
                85                  90                  95

Phe Leu Ser Lys Lys Thr Asp Glu Leu Arg Asn Leu His Lys Leu
            100                 105                 110

Leu Tyr Asn Arg Pro Gly Thr Val Ser Ser Leu Lys Lys Asn Val Gly
        115                 120                 125

Gln Phe Ser Gly Phe Pro Phe Glu Lys Gly Ser Val Gln Tyr Lys Lys
    130                 135                 140

Lys Glu Glu Met Leu Lys Lys Phe Arg Asn Ala Met Leu Lys Ser Ile
145                 150                 155                 160

Cys Glu Val Leu Asp Leu Glu Arg Ser Gly Val Asn Ser Glu Leu Val
                165                 170                 175

Lys Arg Ile Leu Asn Phe Leu Met His Pro Lys Pro Ser Gly Lys Pro
            180                 185                 190

Leu Pro Lys Ser Lys Lys Thr Cys Ser Lys Gly Ser Lys Lys Glu Arg
        195                 200                 205

Asn Ser Ser Gly Met Ala Arg Lys Ala Lys Arg Thr Lys Cys Pro Glu
    210                 215                 220

Ile Leu Ser Asp Glu Ser Ser Asp Glu Asp Glu Lys Lys Asn Lys
225                 230                 235                 240

Glu Glu Ser Ser Asp Asp Glu Asp Lys Glu Ser Glu Glu Glu Pro Pro
                245                 250                 255

Lys Lys Thr Ala Lys Arg Glu Lys Pro Lys Gln Lys Ala Thr Ser Lys
            260                 265                 270

Ser Lys Lys Ser Val Lys Ser Ala Asn Val Lys Lys Ala Asp Ser Ser
        275                 280                 285

Thr Thr Lys Lys Asn Gln Asn Ser Ser Lys Lys Glu Ser Glu Ser Glu
    290                 295                 300

Asp Ser Ser Asp Asp Glu Pro Leu Ile Lys Lys Leu Lys Lys Pro Pro
305                 310                 315                 320

Thr Asp Glu Glu Leu Lys Glu Thr Ile Lys Lys Leu Leu Ala Ser Ala
                325                 330                 335

Asn Leu Glu Glu Val Thr Met Lys Gln Ile Cys Lys Lys Val Tyr Glu
            340                 345                 350

Asn Tyr Pro Thr Tyr Asp Leu Thr Glu Arg Lys Asp Phe Ile Lys Thr
        355                 360                 365

Thr Val Lys Glu Leu Ile Ser
    370                 375

<210> SEQ ID NO 15
<211> LENGTH: 374
<212> TYPE: PRT
<213> ORGANISM: Homo sapiens

<400> SEQUENCE: 15

Met Ser Arg Val Pro Ser Pro Pro Ala Glu Met Ser Ser Gly
1               5                   10                  15

Pro Val Ala Glu Ser Trp Cys Tyr Thr Gln Ile Lys Val Val Lys Phe
            20                  25                  30

Ser Tyr Met Trp Thr Ile Asn Asn Phe Ser Phe Cys Arg Glu Glu Met
        35                  40                  45

Gly Glu Val Ile Lys Ser Ser Thr Phe Ser Ser Gly Ala Asn Asp Lys
    50                  55                  60

Leu Lys Trp Cys Leu Arg Val Asn Pro Lys Gly Leu Asp Glu Glu Ser
65                  70                  75                  80

Lys Asp Tyr Leu Ser Leu Tyr Leu Leu Leu Val Ser Cys Pro Lys Ser
                85                  90                  95

Glu Val Arg Ala Lys Phe Lys Phe Ser Ile Leu Asn Ala Lys Gly Glu
            100                 105                 110

Glu Thr Lys Ala Met Glu Ser Gln Arg Ala Tyr Arg Phe Val Gln Gly
        115                 120                 125

Lys Asp Trp Gly Phe Lys Lys Phe Ile Arg Arg Asp Phe Leu Leu Asp
    130                 135                 140

Glu Ala Asn Gly Leu Leu Pro Asp Asp Lys Leu Thr Leu Phe Cys Glu
145                 150                 155                 160

Val Ser Val Val Gln Asp Ser Val Asn Ile Ser Gly Gln Asn Thr Met
                165                 170                 175

Asn Met Val Lys Val Pro Glu Cys Arg Leu Ala Asp Glu Leu Gly Gly
            180                 185                 190

Leu Trp Glu Asn Ser Arg Phe Thr Asp Cys Cys Leu Cys Val Ala Gly
        195                 200                 205

Gln Glu Phe Gln Ala His Lys Ala Ile Leu Ala Ala Arg Ser Pro Val
    210                 215                 220

Phe Ser Ala Met Phe Glu His Glu Met Glu Glu Ser Lys Lys Asn Arg
225                 230                 235                 240

Val Glu Ile Asn Asp Val Glu Pro Glu Val Phe Lys Glu Met Met Cys
                245                 250                 255

Phe Ile Tyr Thr Gly Lys Ala Pro Asn Leu Asp Lys Met Ala Asp Asp
            260                 265                 270

Leu Leu Ala Ala Ala Asp Lys Tyr Ala Leu Glu Arg Leu Lys Val Met
        275                 280                 285

Cys Glu Asp Ala Leu Cys Ser Asn Leu Ser Val Glu Asn Ala Ala Glu
    290                 295                 300

Ile Leu Ile Leu Ala Asp Leu His Ser Ala Asp Gln Leu Lys Thr Gln
305                 310                 315                 320

Ala Val Asp Phe Ile Asn Tyr His Ala Ser Asp Val Leu Glu Thr Ser
                325                 330                 335

Gly Trp Lys Ser Met Val Val Ser His Pro His Leu Val Ala Glu Ala
            340                 345                 350

```
Tyr Arg Ser Leu Ala Ser Ala Gln Cys Pro Phe Leu Gly Pro Pro Arg
        355                 360                 365

Lys Arg Leu Lys Gln Ser
    370
```